(12) United States Patent
Marsh et al.

(10) Patent No.: US 12,125,574 B2
(45) Date of Patent: Oct. 22, 2024

(54) SYSTEMS AND METHODS FOR PARALLEL PREPARATION PROCESSING

(71) Applicant: Omnicell, Inc., Mountain View, CA (US)

(72) Inventors: Charles Marsh, Cranberry Township, PA (US); Larry McCutchan, Allison Park, PA (US); Ryan Kaintz, Allison Park, PA (US); Ezekiel Braun, Sewickley, PA (US); Walter Petersen, Seattle, WA (US); Robert Eckert, Cranberry Township, PA (US); Robert Barrie Slaymaker, Jr., Pittsburgh, PA (US)

(73) Assignee: Omnicell, Inc., Mountain View, CA (US)

( * ) Notice: Subject to any disclaimer, the term of this patent is extended or adjusted under 35 U.S.C. 154(b) by 1091 days.

(21) Appl. No.: 17/006,027

(22) Filed: Aug. 28, 2020

(65) Prior Publication Data

US 2022/0068457 A1    Mar. 3, 2022

(51) Int. Cl.
*B65B 3/00*        (2006.01)
*A61M 5/20*       (2006.01)
(Continued)

(52) U.S. Cl.
CPC .............. *G16H 20/17* (2018.01); *A61M 5/20* (2013.01); *A61M 5/31* (2013.01); *B65B 3/003* (2013.01);
(Continued)

(58) Field of Classification Search
CPC .......... B65B 3/003; B65B 57/145; A61J 1/06; A61J 1/20; A61J 1/2055; A61J 1/2096;
(Continued)

(56) References Cited

U.S. PATENT DOCUMENTS 4,842,028 A * 6/1989 Kaufman et al. ......... A61J 1/20
                                                                141/330
5,341,854 A * 8/1994 Zezulka et al. ........... A61J 1/20
                                                                141/2

(Continued)

OTHER PUBLICATIONS

International Application No. PCT/US2021/046887 received an International Search Report and Written Opinion, mailed on Nov. 26, 2021, 9 pages.

*Primary Examiner* — Stephen F. Gerrity
(74) *Attorney, Agent, or Firm* — Kilpatrick Townsend & Stockton LLC; Darin Gibby; Richard B. Christiansen

(57) ABSTRACT

Systems and methods for parallel medication processing are disclosed herein. Such methods can include receiving a request for preparation of a plurality of dosed medication delivery containers, determining at least one attribute of the request for preparation of at least one dosed medication delivery container, identifying a template corresponding to the at least one attribute of the request, the template identifying steps and a step sequence for filling the dosed medication delivery container, and executing the template. Executing the template can include iteratively assigning tasks to a plurality of stations within the automated dosing device, the performance of which tasks at least partially overlap, and directing a transport tool to move at least one medication delivery container between the stations of the automated dosing device.

41 Claims, 17 Drawing Sheets

(51) Int. Cl.
*A61M 5/31* (2006.01)
*B65B 57/14* (2006.01)
*G16H 10/60* (2018.01)
*G16H 20/17* (2018.01)
*G16H 40/60* (2018.01)

(52) U.S. Cl.
CPC ........... *B65B 57/145* (2013.01); *G16H 10/60* (2018.01); *G16H 40/60* (2018.01); *A61M 2005/3114* (2013.01)

(58) Field of Classification Search
CPC .... A61J 2200/74; A61J 2205/00; A61M 5/20; A61M 5/31; A61M 2005/3114; G16H 10/60; G16H 20/17; G16H 40/20; G16H 40/60
See application file for complete search history.

(56) References Cited

U.S. PATENT DOCUMENTS

| | | | |
|---|---|---|---|
| 6,837,696 B2 | 1/2005 | Sow den et al. | |
| 7,017,623 B2 | 3/2006 | Tribble et al. | |
| 7,610,115 B2 | 10/2009 | Rob et al. | |
| 8,386,070 B2 | 2/2013 | Eliuk et al. | |
| 10,351,285 B2 | 7/2019 | Sweet et al. | |
| 2015/0251780 A1* | 9/2015 | Matsukuma et al. ... | B65B 3/003 141/2 |
| 2016/0200462 A1* | 7/2016 | Kriheli et al. .......... | B65B 3/003 700/214 |

* cited by examiner

SYSTEMS AND METHODS FOR PARALLEL PREPARATION PROCESSING

CROSS-REFERENCES TO RELATED APPLICATIONS

This application is related to U.S. patent application Ser. No. 17/005,786, filed concurrently herewith and titled "Medication Dosing Systems and Methods"; U.S. patent application Ser. No. 17/005,637, filed concurrently herewith and titled "Bag Transfer Mechanism for IV Compounding"; U.S. patent application Ser. No. 17/005,650, filed concurrently herewith and titled "Cartridge Loading System for Syringe Caps"; and U.S. patent application Ser. No. 17/005,803, filed concurrently herewith and titled "Cabinet with Integrated Pick-and-Place Mechanism"; the disclosures of which are hereby incorporated by reference herein in their entireties for all purposes.

BACKGROUND

Processing, or compounding, of drugs in the modern IV pharmacy involves complex tasks that must be completed under aseptic conditions and with careful record keeping. Automated devices that make this faster, safer and more compliant with regulatory requirements have been devised. First generation pharmacy automation devices could perform only one compounding task, such as filling a syringe, well. This left the preliminary processing to be done manually. With such devices, it is often necessary to prepare a preliminary preparation, such as a stock bag, stock vial or reconstitution, from which the patient doses are drawn to make the final preparations. Second generation automation devices were more flexible, adding hardware and software to make preliminary preparations. Such second generation automation devices provided significant benefit over first generation devices, but are unable to meet demands for higher outputs efficiently. In light of these limitations of pharmacy automation devices, further developments and improvements are desired.

Further, for sterile compounding procedure, maintaining the sterility and cleanliness of critical sites (locations that include any component or fluid pathway surfaces e.g., vial septa, injection ports, or openings e.g., needle hubs that are exposed and at risk of direct contact with air, moisture, or touch contamination) is a primary concern for Compounded Sterile Preparation (CSP). USP 797 Sterile Pharmaceutical Compounding Procedures essentially focuses on maintaining air quality of Class 5 or better in all critical areas of compounding processes.

Current generation pharmacy automation devices only include locating a sampling probe within the compounding area. Further, particle counting monitoring is managed by a customer facility with an independent particle counter connected to the device probe. Currently, there is no mitigation for false counting and there is no control on probe contamination by manual operation for cleaning and maintenance. Additionally, the current implementation does not provide any feedback to the pharmacy automation device to stop or allow compounding.

BRIEF SUMMARY

One aspect of the present disclosure relates to a method of parallel medication processing using an automated dosing device. The method includes receiving a request for preparation of a at least one dosed medication delivery container with the automated dosing device. In some embodiments, each of the at least one dosed medication delivery containers can include a medication delivery container and at least one ingredient added to the medication delivery container by the automated dosing device. In some embodiments, the automated dosing device can include a plurality of stations, and the at least one medication delivery container can be at least one of: a syringe; and a medication bag. The method can include determining at least one attribute of the request for preparation of at least one dosed medication delivery container, and identifying a template corresponding to the determined at least one attribute of the request for preparation of the at least one dosed medication delivery container. In some embodiments, the template identifies steps and an order of the steps for the filling of the dosed medication delivery container. The method includes executing the template which can include iteratively assigning tasks to a plurality of stations within the automated dosing device, and directing a transport tool to move at least one medication delivery container between the stations of the automated dosing device. In some embodiments, at least some of the tasks are at least partially overlappingly performed by a plurality of stations.

In some embodiments, the at least one attribute includes at least one of: a type of the at least one dosed medication delivery container, a number of ingredients in the at least one dosed medication delivery container, a source of at least one of the ingredients in the at least one dosed medication delivery container, and a dose size for each of the ingredients in the at least one dosed medication delivery container. In some embodiments, at least partially overlappingly performing at least some of the tasks includes simultaneously performing at least some of the tasks. In some embodiments, the at least one medication delivery container includes a plurality of individual syringes.

In some embodiments, the transport tool includes a robotic arm that can grab or grip and manipulate the at least one medication delivery container. In some embodiments, the transport tool further includes a bag carousel. In some embodiments, the bag carousel can include a circular member having an outer circumference, a plurality of slots sized to receive a medication bag, and at least one bag shuttle having a moveable member that can remove the medication bag from the bag carousel. In some embodiments, the medication bag received in one of the plurality of slots is wholly retained within the outer circumference of the circular member.

In some embodiments, the plurality of stations include a doser, a scale, at least one reconstitution mixer, a withdrawal station, and a syringe finisher. In some embodiments, the scale can include two or more syringe holders. In some embodiments, the scale further comprises a medication bag holder, and wherein executing the template comprises determining a weight of a medication bag based on a plurality of weights of multiple medication delivery containers measured by the scale, wherein the multiple medication delivery containers include the medication bag and a syringe.

In some embodiments, executing the template includes filling a first syringe with a first medication with the doser, and dosing medication bags with a first medication. In some embodiments, dosing medication bags with the first medication includes transferring a first one of a plurality of medication bags from a bag carousel to the doser, injecting with the first syringe a dose of the first medication into the first one of the plurality of medication bags, transferring the first one of the plurality of medication bags from the doser to the bag carousel, and rotating the bag carousel in a first direction to position a first next one of the plurality of medication bags for transferring from the bag carousel to the doser.

In some embodiments, dosing the medication bags with the first medication includes measuring a first weight of the first one of the plurality of medication bags before injecting with the first syringe the dose of the first medication into the first one of the plurality of medication bags, measuring a second weight of the first one of the plurality of medication bags after injecting with the first syringe the dose of the first medication into the first one of the plurality of medication bags, and determining a dosing of the first one of the plurality of medication bags based on the first weight and the second weight. In some embodiments, executing the template further includes filling a second syringe with a second medication with the doser, and dosing medication bags with the second medication. In some, embodiments, dosing medication bags with the second medication includes transferring a second one of the plurality of medication bags from the bag carousel to the doser, injecting with the second syringe a second dose of the second medication into the second one of the plurality of medication bags, transferring the second one of the plurality of medication bags from the doser to the bag carousel, and rotating the bag carousel in a second direction to position a second next one of the plurality of medication bags for transferring from the bag carousel to the doser. In some embodiments, executing the template includes controlling the transport tool to place an empty, first syringe in a first syringe holder, measuring and storing a first weight with the scale, the first weight corresponding to the weight of the empty, first syringe, controlling the transport tool to place the empty, first syringe in the doser for filling and an empty, second syringe in the first syringe holder, measuring and storing a second weight with the scale, the second weight corresponding to the weight of the empty, second syringe, filling the first syringe with the doser, controlling the transport tool to retrieve the filled, first syringe from the doser and place the filled, first syringe in a second syringe holder, and measuring and storing a third weight with the scale, the third weight corresponding to the weight of the filled, first syringe and of the empty, second syringe.

In some embodiments, executing the template further includes determining a weight of the filled, first syringe by determining a difference between the third weight and the second weight. In some embodiments, executing the template further includes determining a dosing of the first syringe by determining a difference between the weight of the filled, first syringe and the first weight. In some embodiments, the request for preparation of the at least one dosed medication delivery container with the automated dosing device includes a request for preparation of a plurality of dosed medication delivery containers.

In some embodiments, the method includes dividing the request for preparation of the plurality of dosed medication delivery containers into a plurality of mini-batches, and processing each of the mini-batches. In some embodiment processing each of the mini-batches causes preparation of a subset of the plurality of dosed medication delivery containers. In some embodiments, each of the mini-batches can be serially processed. In some embodiments, dividing the request for preparation of the plurality of dosed medication delivery containers into the plurality of mini-batches includes identifying a size for the mini-batches, and creating the plurality of mini-batches of the identified size. In some embodiments, identifying the size for the mini-batches includes identifying ingredients and dosing of the ingredients for preparation of each of the plurality of dosed medication delivery containers, identifying a vial size for each of the ingredients, determining a maximum number of doses for each of the ingredients, and setting the size for the mini-batch at the largest of the maximum number of doses for each of the ingredients.

One aspect of the present disclosure relates to an automated dosing device. The automated dosing device can include a plurality of stations, each of the plurality of stations can include a station controller and station hardware, and each station controller can control station hardware to perform an operation. The automated dosing device can include a transport tool that can transport medication delivery containers to and from the plurality of stations. The automated dosing device includes a central controller including a processor. The processor can receive a request for preparation of at least one dosed medication delivery container, each of the at least one dosed medication delivery container including a medication delivery container at least partially filled by at least one ingredient. In some embodiments, the medication delivery container includes at least one of: a syringe and a medication bag. The processor can determine at least one attribute of the request for preparation of at least one dosed medication delivery container, and identify a template corresponding to the determined at least one attribute of the request for preparation of the at least one dosed medication delivery container, which template identifies steps and an order of the steps for the filling of the dosed medication delivery container. The processor can execute the template, which executing of the template can include iteratively assigning tasks to at least some of the plurality of stations, at least some of which tasks are at least partially overlappingly performed, and directing a transport tool to move at least one medication delivery container between the stations.

In some embodiments, the at least one attribute includes at least one of a type of the at least one dosed medication delivery container, a number of ingredients in the at least one dosed medication delivery container, a source of at least one of the ingredients in the at least one dosed medication delivery container, and a dose size for each of the ingredients in the at least one dosed medication delivery container. In some embodiments, at least partially overlappingly performing at least some of the tasks includes simultaneously performing at least some of the tasks.

In some embodiments, the at least one medication delivery container can include a plurality of individual syringes. In some embodiments, the transport tool includes a robotic arm that can grab or grip and manipulate the at least one medication delivery container, and a bag carousel. In some embodiments, the bag carousel can include circular member having an outer circumference, a plurality of slots sized to receive a medication bag, and at least one bag shuttle including a moveable member that can remove the medication bag from the bag carousel. In some embodiments, the medication bag received in one of the plurality of slots is wholly retained within the outer circumference of the circular member.

In some embodiments, the plurality of stations include a doser, a scale, at least one reconstitution mixer, a withdrawal station, and a syringe finisher. In some embodiments, the scale includes two or more syringe holders. In some embodiments, the scale further includes a medication bag holder. In some embodiments, executing the template includes determining a weight of a medication bag based on a plurality of weights of multiple medication delivery containers measured by the scale. In some embodiments, the multiple medication delivery containers include the medication bag and the syringe.

In some embodiments, executing the template includes filling a first syringe with a first medication with the doser, and dosing medication bags with a first medication. In some embodiments, dosing medication bags with the first medication includes transferring a first one of a plurality of medication bags from the bag carousel to the doser, injecting with the first syringe a dose of the first medication into the first one of the plurality of medication bags, transferring the first one of the plurality of medication bags from the doser to the bag carousel, and rotating the bag carousel in a first direction to position a first next one of the plurality of medication bags for transferring from the bag carousel to the doser. In some embodiments, dosing the medication bags with the first medication includes measuring a first weight of the first one of the plurality of medication bags before injecting with the first syringe the dose of the first medication into the first one of the plurality of medication bags, measuring a second weight of the first one of the plurality of medication bags after injecting with the first syringe the dose of the first medication into the first one of the plurality of medication bags, and determining a dosing of the first one of the plurality of medication bags based on the first weight and the second weight.

In some embodiments, executing the template further includes filling a second syringe with a second medication with the doser, and dosing medication bags with the second medication. In some embodiments, dosing medication bags with the second medication includes transferring a second one of the plurality of medication bags from the bag carousel to the doser, injecting with the second syringe a second dose of the second medication into the second one of the plurality of medication bags, transferring the second one of the plurality of medication bags from the doser to the bag carousel, and rotating the bag carousel in a second direction to position a second next one of the plurality of medication bags for transferring from the bag carousel to the doser.

In some embodiments, executing the template includes controlling the transport tool to place an empty, first syringe in a first syringe holder, measuring and storing a first weight with the scale, the first weight corresponding to the weight of the empty, first syringe, controlling the transport tool to place the empty, first syringe in the doser for filling and an empty, second syringe in the first syringe holder, measuring and storing a second weight with the scale, the second weight corresponding to the weight of the empty, second syringe, filling the first syringe with the doser, controlling the transport tool to retrieve the filled, first syringe from the doser and place the filled, first syringe in the second syringe holder, and measuring and storing a third weight with the scale, the third weight corresponding to the weight of the filled, first syringe and of the empty, second syringe. In some embodiments, executing the template further includes determining a weight of the filled, first syringe by determining a difference between the third weight and the second weight. In some embodiments, executing the template further includes determining a dosing of the first syringe by determining a difference between the weight of the filled, first syringe and the first weight.

In some embodiments, the request for preparation of the at least one dosed medication delivery container includes a request for preparation of a plurality of dosed medication delivery containers. In some embodiments, the processor can divide the request for preparation of the plurality of dosed medication delivery containers into a plurality of mini-batches, and direct processing each of the mini-batches. In some embodiments, processing each of the mini-batches causes preparation of a subset of the plurality of dosed medication delivery containers. In some embodiments, each of the mini-batches are serially processed. In some embodiments, dividing the request for preparation of the plurality of dosed medication delivery containers into the plurality of mini-batches includes: identifying a size for the mini-batches, and creating the plurality of mini-batches of the identified size. In some embodiments, identifying the size for the mini-batches includes identifying ingredients and dosing of the ingredients for preparation of each of the plurality of dosed medication delivery containers, identifying a vial size for each of the ingredients, determining a maximum number of doses for each of the ingredients, and setting the size for the mini-batch at the largest of the maximum number of doses for each of the ingredients.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label. Additionally, where similar components include the same first reference label, the similar components may have similar structure and operation except where explicitly stated otherwise.

DETAILED DESCRIPTION

Figure 1:
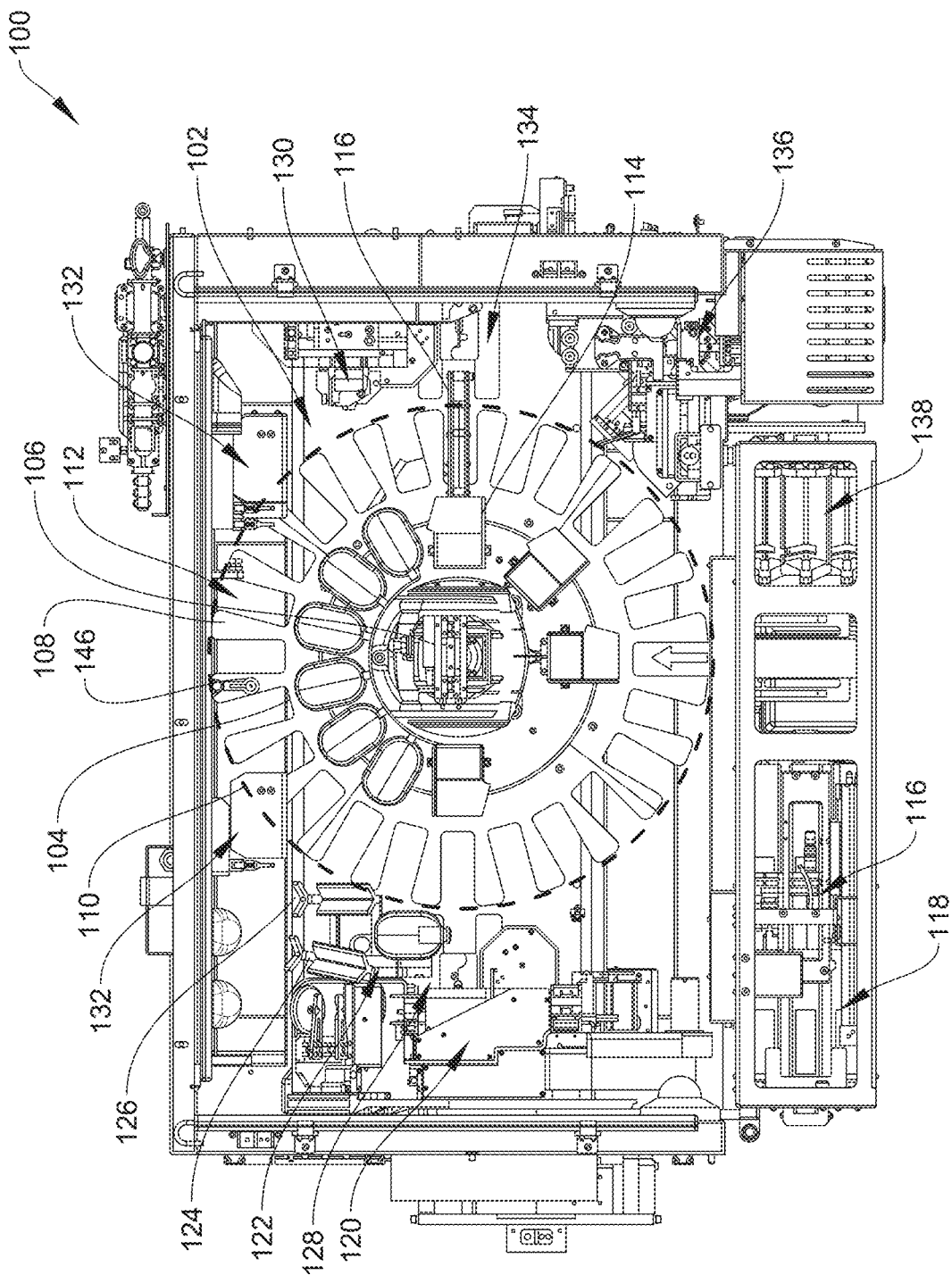
FIG. 1 is a top view of one embodiment of an automated dosing device.

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It will be understood that various changes may be made in the function and arrangement of elements without departing from the spirit and scope of the invention as set forth in the appended claims. Merely by way of example, any embodiment described herein may or may not have any of the features discussed therewith, and may or may not have any feature discussed with respect to other embodiments.

Some embodiments of the present disclosure are directed at automated dosing devices that provide for parallel processing to increase outputs and efficiency. Some exemplary embodiments of the present disclosure are directed to automated dosing mechanisms that facilitate high speed, accurate fluid transfer processes. These high speed, accurate fluid transfer processes enable the higher and/or more efficient output of dosed medication delivery containers. As used herein, a "medication delivery container" can include any container such as a syringe, a medication bag such as an IV bag or any other container used for intravenous infusion, or the like, that has not yet completed operations by the automated dosing device to add one or several ingredients, which can include one or several medications, to the medication delivery container. In some embodiments, the syringes can be independent syringes, also referred to herein individual syringes, which independent syringes are not connected to each other. As used herein, a "dosed medication delivery container" is a medication delivery container that has completed operations by the automated dosing device to add on ore several ingredients, which ingredients can include one or several medications, to the medication delivery container, and which medication delivery container has been made available for use. The medication delivery container is made available for use when the automated dosing device determines that all requested operations have been performed for that medication delivery container, and in some embodiments, that medication delivery container can be placed in a "pick-up" location or other location for retrieval of dosed medication delivery containers.

In some embodiments, for example, an automated dosing device can be a multi-station device, which stations can perform distinct tasks. A central controller can coordinate operations of these stations to create the dosed medication delivery containers. In some embodiments, the central controller can control the stations such that multiple stations of the automated dosing device operate in parallel, thereby decreasing the time to complete the dosing of one or several medication delivery containers.

In some embodiments, each of some or all of these stations can include a station controller. The station controller for a station can control the operation of that station. In some embodiments, the station controller can receive a signal, communication, and/or instruction from the central controller, which signal, communication, and/or instruction can trigger the station controller to cause the station to proceed through one or several operations. By splitting control between the central controller and the station controller, the functioning of individual stations is not as dependent on the processing load on central controller, or in other words, high processing demands on the central controller do not readily interfere with the operation of individual stations. Further, independent station controllers increase the reliability and robustness of the automated dosing device.

The automated dosing device can further include one or several transport tools that can facilitate parallel medication processing. These transport tools can include, for example, a robotic arm and/or bag carousel. Each of the robotic arm and the bag carousel can move one or several objects between stations in the automated dosing device. Specifically, the robotic arm can move one or several vials and/or syringes to and/or from stations within the automated dosing device, and the bag carousel can move one or several medication bags to and/or from one or several stations in the automated dosing device. These stations can include features to hold and/or retain the received one or several medication bags, vials, and/or syringes. These features can include, for example, one or several containers, grippers, holders or the like. As these objects can be held and/or retained by features of the station to which they are delivered, as opposed to by the robotic arm and/or bag carousel, the robotic arm and/or the bag carousel are free to perform other operations after delivering an object to a station. By freeing the robotic arm and/or bag carousel from holding objects at a station while the station operation is being performed, the automated dosing device is able to perform operations in parallel across multiple stations.

The central controller of the automated dosing device can control stations of the automated dosing device according to a selected one of a plurality of templates, which selected one of the plurality of templates corresponds to one or several attributes of a request received by the central controller. These attributes can include, for example, a type of the medication delivery container, the number of operations to be performed for creation of each of the dosed medication delivery containers, a source of one or more of the ingredients used in the creation of the dosed medication delivery containers, and/or a dose size for each of the ingredients used in the creation of the dosed medication delivery container. Based on these attributes, the central controller can identify and retrieve a corresponding template and can execute this template to thereby control the stations of the automated dosing device to thereby create one or several dosed medication delivery containers.

With reference now to FIG. 1, a top view of one embodiment of an automated dosing device 100 is shown. The automated dosing device 100 can prepare a plurality of dosed medication delivery containers. In some embodiments, the automated dosing device 100 can use parallel processing, also referred to herein as parallel medication processing, to prepare a plurality of dosed medication delivery containers.

The automated dosing device 100 includes a transport tool 102 that can move one or several medication delivery containers to and/or from one or several stations within the automated dosing device 100. The transport tool 102 can include the bag carousel 104 and the robotic arm 106. The bag carousel 104 can move medication delivery containers, and specifically medication bags, between stations of the automated dosing device 100, and the robotic arm 106 can move medication delivery containers, and specifically syringes and/or vials, between stations of the automated dosing device 100. In some embodiments, the bag carousel 104 and the robotic arm 106 can operate independently of each other, and in some embodiments, the bag carousel 104 and the robotic arm 106 can at least partially overlappingly move medication delivery containers to and/or from stations within the automated dosing device 100, and in some embodiments, the bag carousel 104 and the robotic arm 106 can simultaneously move medication delivery containers to and/or from stations within the automated dosing device 100. The robotic arm 106 can be configured to grab and manipulate medication delivery containers, and in some embodiments, the robotic arm can include a gripper comprising one or several mechanisms that can grip objects. These mechanisms can include, for example, a pincer-like device, fingers, one or several vacuum cups, or the like. In some embodiments, these mechanisms can include a combination of two or more of: a pincer-like device; fingers; and one or more suctions cups.

The bag carousel 104 can comprise a circular member 108 having an outer circumference 110 and defining a plurality of slots 112. The slots 112 are sized to receive a medication bag, and specifically to receive a medication bag such that the medication bag is wholly retained within the outer circumference 110 of the circular member 108. The bag carousel 104 further includes at least one bag shuttle 114 comprising a moveable member 116. The bag shuttle 114, and specifically the moveable member 116 can remove the medication bag from the bag carousel 104, and specifically can push the medication bag from the slot 112 retaining the medication bag.

These stations can include a decap and vision station 116, a syringe carousel 118, a doser 120, a scale 122, a reconstitution module 130, a reconstitution mixer 132, a withdrawal module 134, a syringe finisher 136, and a vial carousel 138. Each of these stations can, in some embodiments, include a station controller that can comprises a processor and associated memory. The station controller of each station can control one or several hardware components of that station to perform an operation.

The automated dosing device 100 can include a syringe decap and vision module 116. The syringe decap and vision module 116 can receive syringes, decap the syringes, and visually inspect the received syringes. In some embodiments, this visual inspection can be performed with one or several cameras and/or scanners, and software that, when executed, analyzes image and/or video data generated by the one or several cameras and/or scanners. Syringes can be stored on a syringe carousel 118. The syringe carousel 118 can include multiple positions rotatable about an axis, each of which positions can hold a syringe. The robotic arm 106 can access the syringe carousel 118 to retrieve a syringe from the syringe carousel 118.

The automated dosing device 100 can include a doser 120. The doser 120 can load a syringe from a vial, and in some embodiments, can inject a dose of medication from a syringe into a medication bag. As used herein, a vial includes a bottle or a stock bag. Details of the doser 120 are disclosed in U.S. patent application Ser. No. 17/005,786, filed concurrently herewith and titled "Medication Dosing Systems and Methods", the entirety of which is hereby incorporated by reference herein.

The automated dosing device 100 can include a scale 122. The scale 122 can weigh one or several medication delivery devices. The scale 122 can include two or more syringe holders, and specifically can include a first syringe holder 124 and a second syringe holder 126. In some embodiments, the scale 122 can further include a medication bag holder 128. The syringe holders 124, 126 can each receive and hold a syringe, and the medication bag holder 128 can receive and hold a syringe. In some embodiments, all of the syringe holders 124, 126 and the bag holder 128 are connected to a single, common scale. Via the collection of multiple measurements and different times, the weight of different syringes and medication bags can be determined. Details of this determination process will be discussed at length below.

The automated dosing device 100 can include a reconstitution module 130. The reconstitution module 130 can include a reconstitution injector 300 (shown in FIG. 3) that can add a sterile diluent, such as, in some embodiments, saline, to a powdered medication contained within a vial. As will be discussed in more detail below with respect to FIG. 3, the reconstitution module 130 can include a vial holder that can receive a vial from the robotic arm 106 and retain that vial. The reconstitution module 130 can further include an injector head that can pierce a septum of the vial and inject the diluent into the vial.

Figure 4:
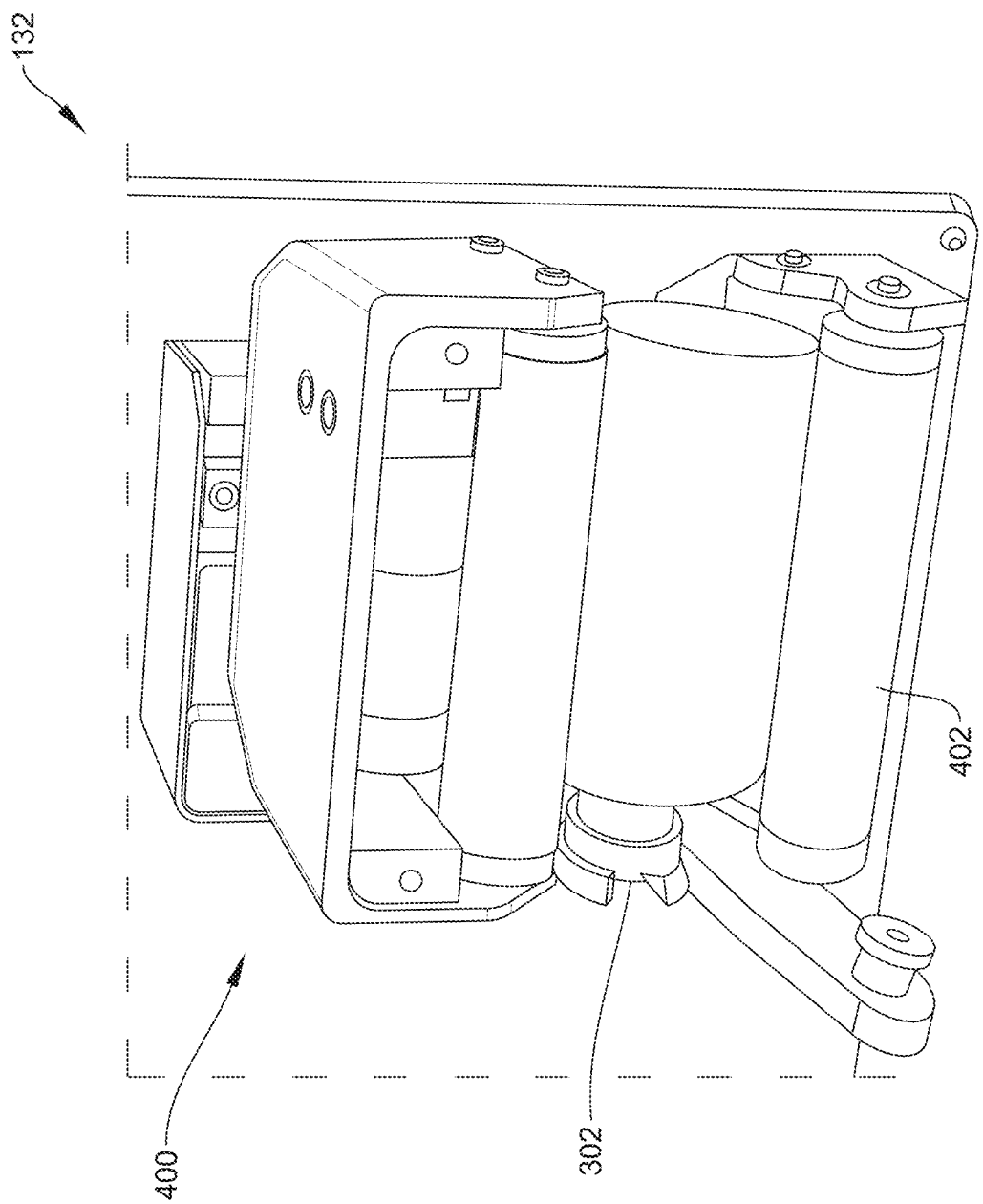
FIG. 4 is a perspective view of one embodiment of a reconstitution mixer.

The automated dosing device 100 can include one or several reconstitution mixers 132. A reconstitution mixer 132 can receive a vial via the robotic arm 106 from the reconstitution module 130. One embodiment of such a reconstitution mixer 132 is shown in FIG. 4. The reconstitution mixer 132 can manipulate the vial to facilitate dissolving of any powdered medication remaining in the vial. The reconstitution mixer 132 can include features that manipulate the vial to facilitate this dissolution. These features can include, for example, one or several rollers, a shaking or vibrating feature, or the like.

The automated dosing device 100 can include a withdrawal module 134. The withdrawal module 134 can, in some embodiments, remove diluent from a medication bag before the addition of any medication to the medication bag by the doser 120. In some embodiments, this removal of diluent from the medication bag can limit the total amount of liquid in the dosed medication bag.

The automated dosing device 100 can include a syringe finisher 136. The syringe finisher 136 can, in some embodiments, remove a needle from the syringe, install a tamper-evident cap on the syringe, and print and apply a label to the syringe. Upon completion of its operations, the syringe finisher 136 can drop a completed syringe into an output bin.

The automated dosing device 100 can include a vial carousel 138. Vials can be stored on the vial carousel 138. The vial carousel 138 can include multiple positions rotatable about an axis, each of which positions can hold a vial. The robotic arm 106 can access the vial carousel 138 to retrieve a vial from the vial carousel 138. In some embodiments, these vials can include powdered medication, reconstituted medication, liquid medication, or any other form of medication.

The automated dosing device 100 can, in some embodiments, include a particle counter probe 146. The particle counter probe 146 can be positioned within a direct compounding area (DCA) 142 (shown in FIG. 2) of the automated dosing device 100, and in some embodiments, can be positioned on a back wall of the automated dosing device 100 as shown in FIG. 1. The DCA 142 can be an area controlled by an ISO Class 5 spec, which area contains critical sites that are exposed to unidirectional HEPA-filtered air, also known as first air. As used herein, "first air" can be air exiting the High Efficiency Particulate Air Filter (HEPA) filter in a unidirectional air stream, until initial interaction with a disturbing object that is essentially particle free. The particle counter probe 146 can collect air samples from within the DCA 142 and can provide these air samples to a particle counter sensor unit 148 (shown in FIG. 2).

Figure 2:
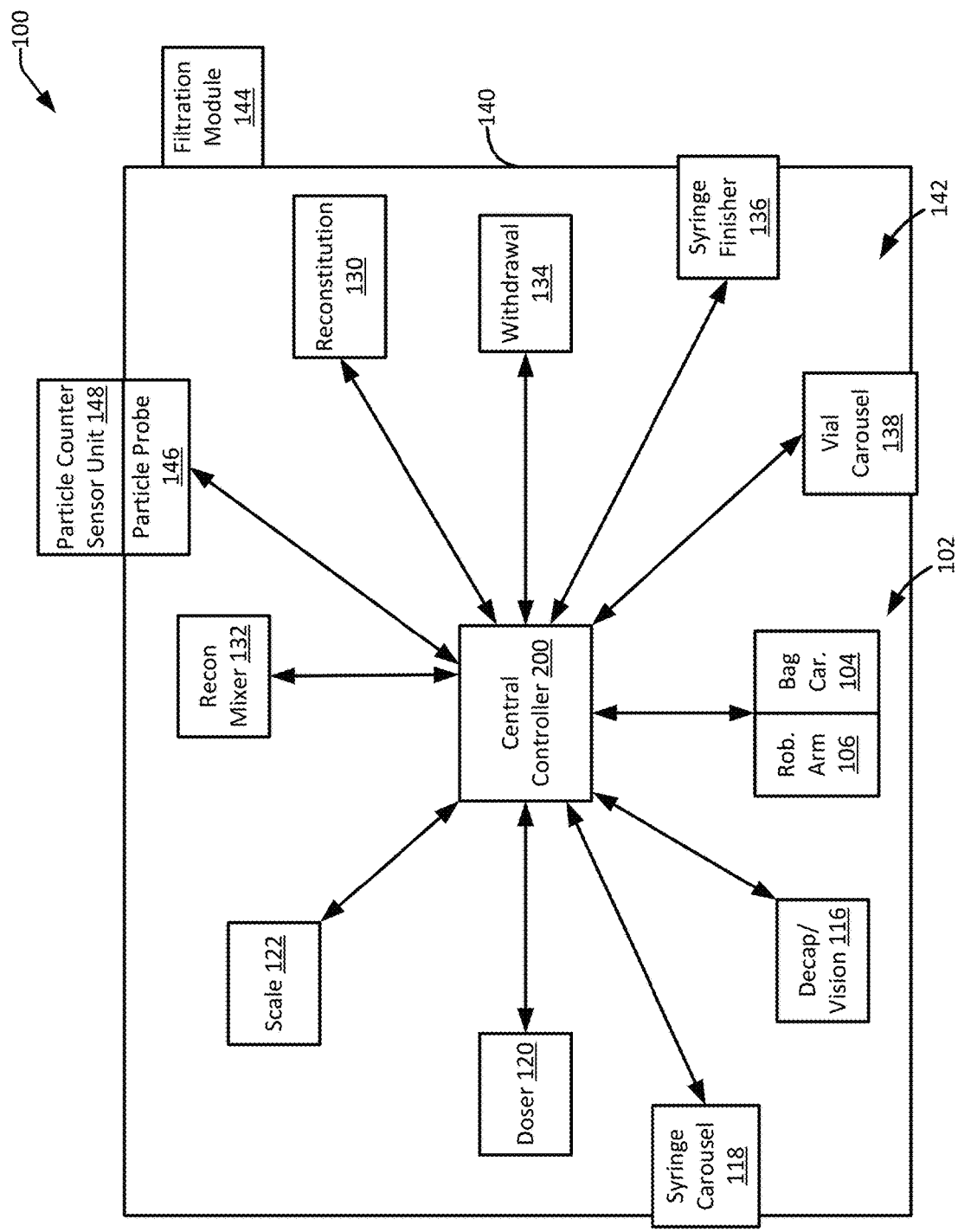
FIG. 2 is a schematic illustration of one embodiment of the automated dosing device.

With reference now to FIG. 2, a schematic illustration of one embodiment of the automated dosing device 100 is shown. The automated dosing device 100 includes the modules and features discussed above with respect to FIG. 1, and further includes a central controller 200. The central controller 200 can comprise one or several computers, servers, processors, or the like. In some embodiments, the central controller 200 can comprise a processor such as a central processing unit and memory. The processor can be, for example, a commercially available microprocessor and/or computer chip. The memory can store instructions in the form of computer code which can be executed by the processor.

In some embodiments, the memory can further store a plurality of templates, each of which templates can comprise an ordered series of instructions for controlling operation of the stations of the automated dosing device 100 to create a desired dosed medication delivery container. A template can be specific to one or several attributes of a dosed medication delivery container. For example, a template may be associated with one or several attributes of a dosed medication delivery container including, for example, a type of the medication delivery container, a number of ingredients to be combined in the dosed medication delivery container, a source of at least one of the ingredients to be combined in the dosed medication delivery container, and a dose size for each of the ingredients to be combined in the dosed medication delivery container.

The template can, in some embodiments, be a data description of processing operations and/or corresponding data embodying the template. In some embodiments, the template can comprises a piece of executable software, which executable software can comprise one or several executable routines and/or sub-routines. In some embodiments, the template can comprise a software script and/or scripting language that embodies the template.

In some embodiments, the template can comprise a static piece of software, and in some embodiments, the template can be a dynamic piece of software. For example, the template can be flexible which can enable the template to react to different situations arising during operation of the automated dosing device 100. If the template was flexible, then it could handle/react to different situations that would impact the compounding process. In such embodiments, the template can morph or change over time, either before execution or during execution. In some embodiments, this morphing or charging can occur, for example, due to one or several of: a condition of the system: such as a subsystem that is not performing adequately or not functioning in as intended; a condition of the system: such as environmental, cleaning, a situation that may cause cross contamination, sterility or any other condition that may limit the template; a condition of the one or several medications within the system including but not limited to expiration, beyond use dating, number of vial piercings, volume of medication, and/or concentration of medication; batch size; pharmacy hours of operation or other operational constraints; and loaded disposables (syringes, bags, tubing sets) or medications.

In some embodiments, the central controller 200 can, upon receiving a request for preparation of a plurality of dosed medication delivery containers, identify a template corresponding to one or several attributes of the request for preparation of the plurality of medication delivery containers. This template can, in some embodiments, identify steps and an order of the steps for the filling of the medication delivery container and/or for the performing of operations on the medication delivery container by the automated dosing device 100.

The central controller 200 can then execute the template, which can include iteratively assigning tasks to stations of the automated dosing device 100. The central controller 200 can further direct the transporter tool 102, which can include directing one or both of the bag carousel 104 and the robotic arm 106, to move medication delivery containers between the stations of the automated dosing device 100. In some embodiments, at least some of the tasks can be at least partially overlappingly performed by the stations, or in other words, multiple stations can be performing distinct task leading to the creation of the dosed medication delivery container. In some embodiments, multiple stations can simultaneously perform at least some tasks for creating the dosed medication delivery container.

In some embodiments, the automated dosing device 100 can serially execute the templates, and in some embodiments such that the automated dosing device does not begin execution of a next template until the execution of a previous template is complete. In some embodiments, two or more templates can be executed wholly or partially in parallel.

The automated dosing device 100 can include a housing 140 that can extend around an area containing some or all of the stations of the automated dosing device 100. The housing 140 can bound the DCA 142. In some embodiments, some stations cross and/or partially cross the housing 140. These stations can, for example, include the syringe carousel 118, the syringe finisher 136, and/or the vial carousel 138. In some embodiments, some or all of these stations can cross the housing and/or partially cross the housing 140 to allow, for example, a user to load one or several syringes and/or vials into the automated dosing device 100 for use by the automated dosing device 100 in creating the dosed medication delivery containers. In some embodiments, the syringe finisher 136 can cross and/or partially cross the housing 140 to allow completed syringes to exit the automated dosing device 100. In some embodiments, a medication bag loader/unloader can cross and/or partially cross the housing 140 to allow the loading of medication bags to the bag carousel 104 and/or the unloading of the medication bags from the bag carousel 104.

The automated dosing device 100 can include a filtration module 144. The filtration module 144 can filter air before the air enters into the DCA 142. The filtration module 144 can comprise a plurality of filters including, for example, one or several pre-filters, one or several post-filters, and/or one or several HEPA filters. The filters can remove particulate and/or contaminants from the air entering into the DCA 142 such that the DCA 142 may be maintained at a desired cleanliness and/or contamination level such as is specified by, for example, a commercial standard such as ISO 14644-1:2015, class 5.

The automated dosing device 100 can include the particle probe 146 and the particle counter sensor unit 148. As mentioned, the particle probe 146 can collect air samples within the DCA 142 and can provide these air samples to the particle counter sensor unit 148. In some embodiments, the particle counter sensor unit 148 can be located outside of the housing 140 and outside of the DCA 142.

Figure 12:
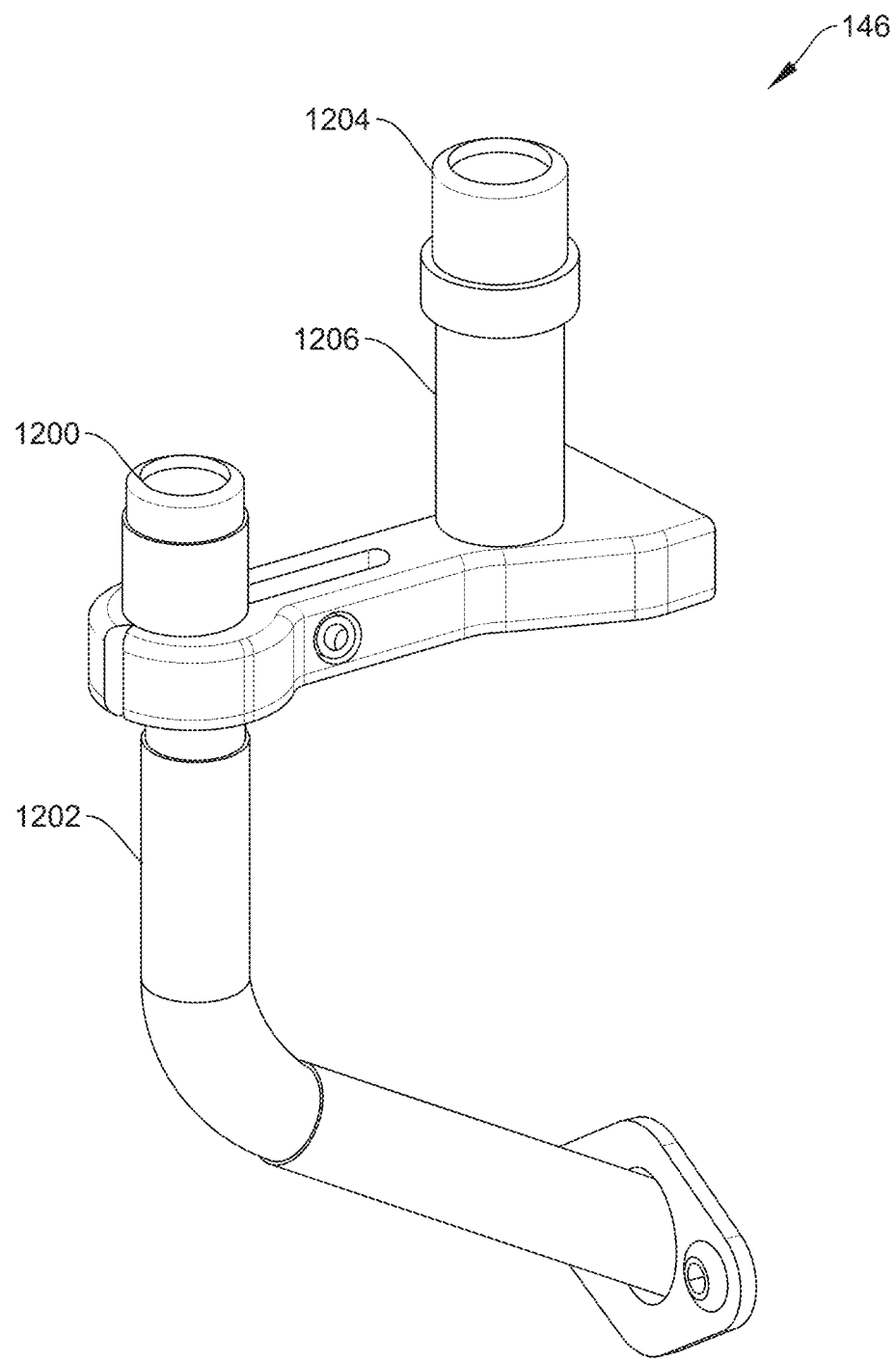
FIG. 12 is a perspective view of one embodiment of a probe.

One embodiment of the particle probe 146 is shown in FIG. 12. The particle probe 146 can include an inlet 1200 coupled to a tube 1202. In some embodiments, the tube 1202 can be coupled to the particle counter sensor unit 148, and specifically can be fluidly coupled to the particle counter sensor unit 148 such that an air sample can enter the inlet 1200 of the particle probe 146 and can pass through the tube 1202 to the particle counter sensor unit 148.

The particle probe 146 can further include a cap 1204 and a cap holder 1206, also referred to herein as a cap rest 1206. In some embodiments, the cap 1204 can be moveable between the inlet 1200 and the cap holder 1206. Specifically, the cap 1204 can be moveable by the robotic arm 106 between the inlet 1200 and the cap holder 1206. In such an embodiment, the robotic arm 106 can grip the cap 1204, and can then move and/or manipulate the cap 1204.

In some embodiments, the cap 1204 can be removed from the inlet 1200 and placed on the cap holder 1206 when a sample is to be collected, and the cap 1204 can be removed from the cap holder 1206 and can be returned to the inlet 1200 when the air sample has been collected and/or when sampling is completed. When placed on the inlet 1200, the cap 1204 can seal the inlet 1200 to prevent air from entering the inlet 1200.

Figure 3:
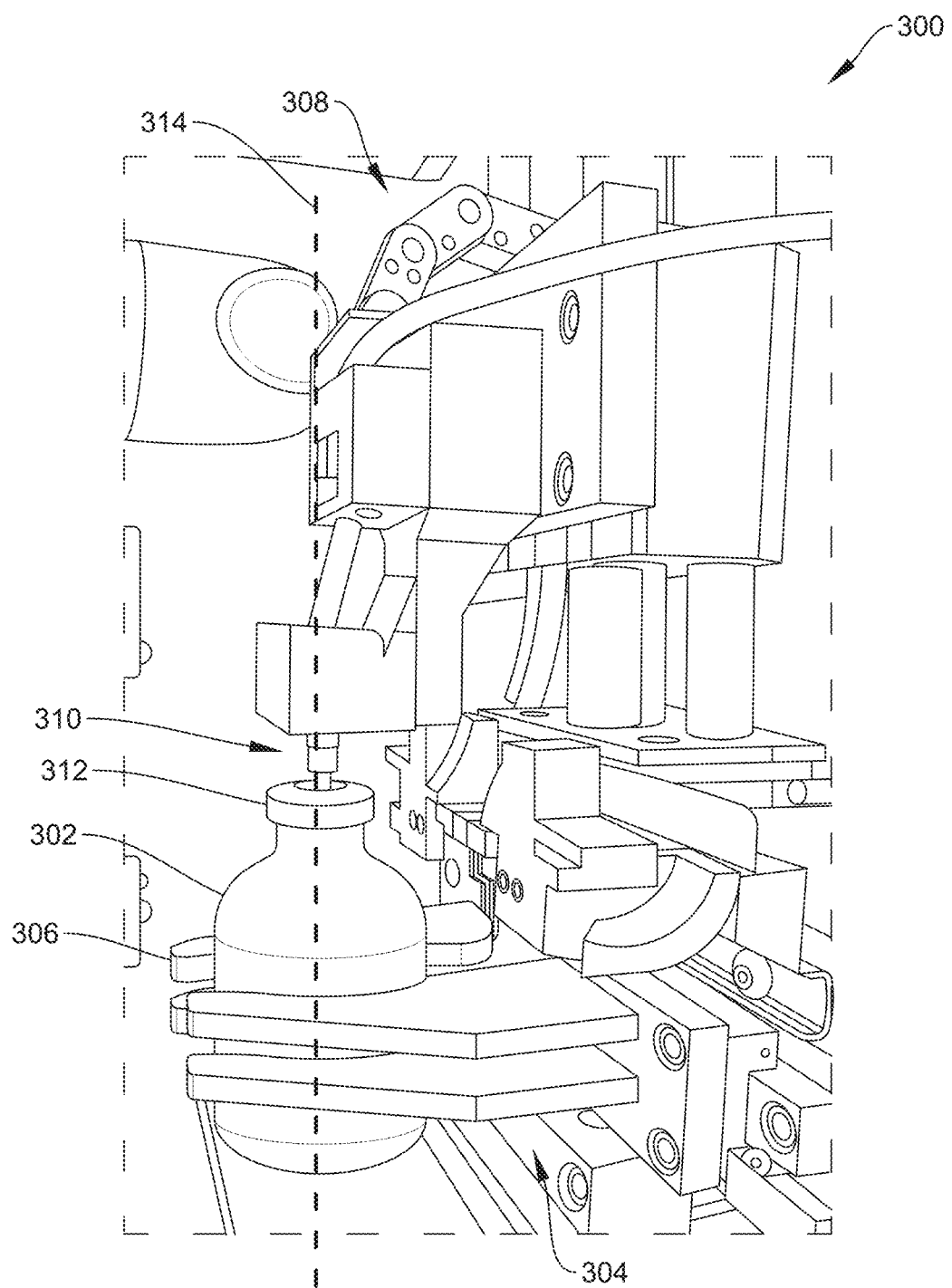
FIG. 3 is a perspective view of one embodiment of the reconstitution injector.

With reference now to FIG. 3, a perspective view of one embodiment of the reconstitution injector 300 is shown. As discussed above, the reconstitution injector 300 can add a sterile diluent, such as, in some embodiments, saline, to a powdered medication contained within a vial 302. The reconstitution injector 300 can include a vial holder 304 that can receive a vial 302 from the robotic arm 106 and retain that vial 302. The vial holder 304 can comprise gripping fingers 306 that can clamp on the vial 302 and/or close around the vial 302. The vial holder 304 can facilitate parallel processing by freeing the robotic arm 106 from holding vials 302 for reconstitution by the reconstitution injector 300. Rather, the robotic arm 106 can deliver the vial 302 to the reconstitution injector 300, which vial 302 can be held by the vial holder 304 during the reconstitution, and the robotic arm can perform other tasks during this reconstitution.

The reconstitution injector 300 can further include an injector head 308 that can pierce a septum of the vial 302 with a piercing/penetrating member 310. This piercing/penetrating member 310 of the injector head 308 can comprise, for example, a needle. In some embodiments, and as depicted in FIG. 3, which septum can be located in a cap 312 of the vial 302. The injector head 308 can inject the diluent into the vial 302 via the piercing/penetrating member 310.

In some embodiments, the injector head 308 and/or the vial holder 304 are moveable with respect to each other. In some embodiments, for example, the vial holder 304 is fixed and the injector head 308 is displaceable, and specifically, linearly displaceable with respect to the vial holder 304. In some embodiments, when a vial 302 is held within the vial holder 304, as depicted in FIG. 3, the injector head 308 is displaceable along axis 314. In some embodiments, displacement along axis 314 results in the piercing/penetrating member 310 penetrating the septum of the vial 302 to enable injection of diluent into the vial 302.

With reference now to FIG. 4, one embodiment of a reconstitution mixer 132 is shown. The reconstitution mixer 132 includes an agitation module 400 that can receive the vial 302 via the robotic arm 106 from the reconstitution module 130. The agitation module 400 can include features that can receive, secure, and/or agitate the vial 302. This agitation can facilitate in the dissolving of medication into the diluent within the vial 320. In the embodiment of the agitation module 400 shown in FIG. 4, the agitation module 400 includes a plurality of rollers 402, and specifically four rollers 402. The vial 302, as shown in FIG. 4, is received in a space between these four rollers 402 and is thereby secured within the agitation module 400. At least one of the rollers 402 of the agitation module 400 can be driven and/or motorized. In such an embodiment, upon receipt of a vial 302 by the agitation module 400, that driven and/or motorized roller 402 can be driven to thereby cause the spinning of the vial 302 within the rollers 402.

In some embodiments, the agitation module 400 can agitate the vial 302 for a predetermined time period and/or according to a predetermined agitation program. In some embodiments, the agitation module 400 can further include one or several sensors which can be used to determine completion of agitation of the vial 302. Specifically, these one or several sensors can detect undissolved medication within the vial 302, and the agitation of the vial 302 can continue until all of the medication is dissolved and/or until the undissolved portion of the medication within the vial 302 falls below a threshold value.

Figure 5:
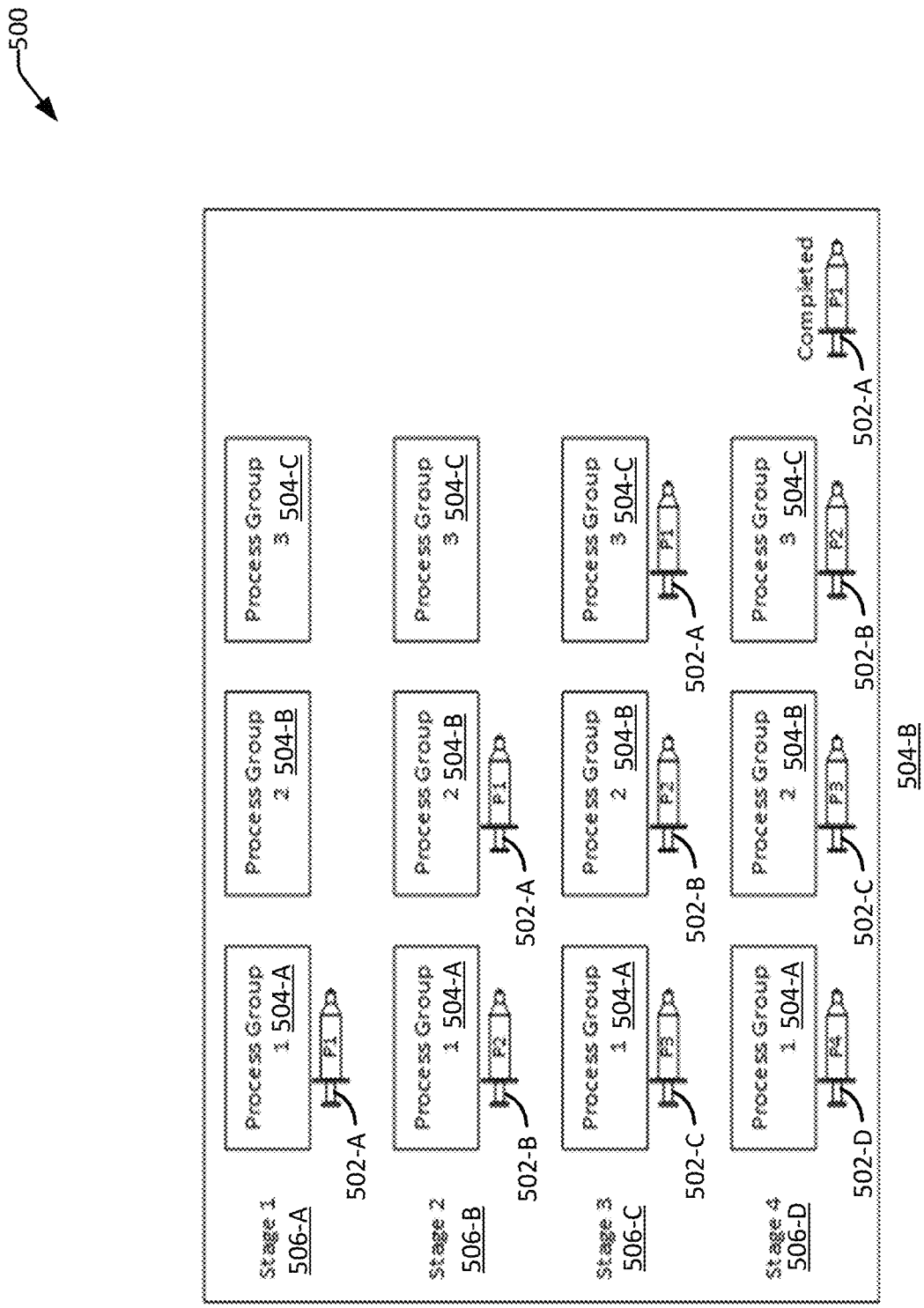
FIG. 5 is a schematic illustration of high-level parallel processing.

With reference now to FIG. 5, a schematic illustration of high-level parallel processing 500 is shown. In the illustrations, medical delivery containers 502 are advanced between process groups corresponding to stations 504 of the automated dosing device 100. The stages 506 correspond to times in the processing of the medical delivery containers 502.

Processing begins with the delivery of the first medication delivery container 502-A to first station 504-A by the robotic arm 106. At stage 1 506-A the first station 504-A performs an operation on the first medication delivery container 502-A. After processing at the first station 504-A is complete, the robotic arm 106 transports the first medication delivery container 502-A to the second station 504-B. The second station 504-B performs an operation on the first medication delivery container 502-A. After delivery of the first medication delivery container 502-A to the second station 504-B, the robotic arm 106 delivers a second medication delivery container 502-B to the first station 504-A, where the first station 504-A performs its operation on the second medication delivery container 502-B. The processing of the first station 504-A and the second station 504-B at stage 2 506-B can be at least partially overlapping and in some embodiments can be simultaneous.

After the completion of the processing of the first medication delivery container 502-A by the second station 504-B and the completion of the processing of the second medication delivery container 502-B by the first station 504-A, the robotic arm 106 transports the first medication delivery container 502-A to the third station 504-C, then transports the second medication delivery container 502-B to the second station 504-B, and transports the third medication delivery container 502-C to the first station 504-A. At stage 3 506-C, and upon receipt of their respective medication delivery containers 502-A, 502-B, 502-C, the stations 504-A, 504-B, 504-C perform their operation on their received one of medication delivery containers 502-A, 502-B, 502-C. The processing of stations 504-A, 504-B, 504-C can be at least partially overlapping and in some embodiments can be simultaneous.

After the completion of the processing of the received first, second, and third medication delivery containers 502-A, 502-B, 502-C by the first, second, and third stations 504-A, 504-B, 504-C, the robotic arm 106 can advance each of the first, second, and third medication delivery containers 502-A, 502-B, 502-C one station. This results in the first medication delivery container 502-A being removed from the third station 504-C and being placed the location for dosed medication delivery containers, the second medication delivery container 502-B being advanced from the second station 504-B to the third station 504-C, the third medication delivery container 502-C being advanced from the first station 504-A to the second station 504-B, and a fourth medication delivery container 502-D being transported to the first station 504-A. At stage 4 506-D, and upon receipt of their respective medication delivery containers 502-B, 502-C, 502-D the stations 504-A, 504-B, 504-C perform their operation on their received one of medication delivery containers 502-B, 502-C, 502-D C. The processing of stations 504-A, 504-B, 504-C can be at least partially overlapping and in some embodiments can be simultaneous.

Such parallel processing of medication delivery containers can be performed until a desired number of dosed medication delivery containers have been created.

Figure 6:
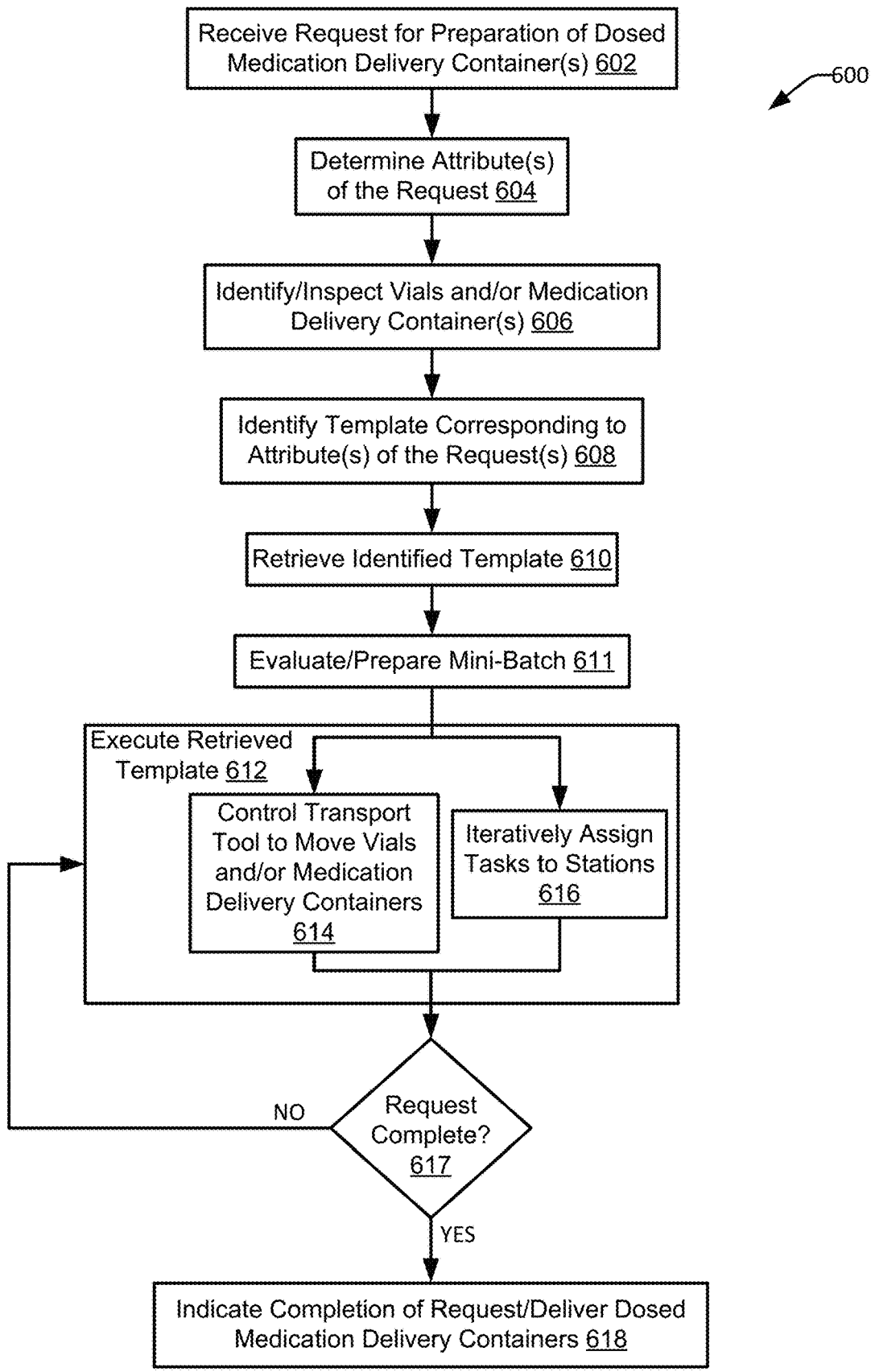
FIG. 6 is a flowchart illustrating one embodiment of a process for parallel medication processing.

With reference now to FIG. 6, a flowchart illustrating one embodiment of a process 600 for parallel medication processing is shown. The process 600 can be performed, in some embodiments, by the automated dosing device 100. The process 600 begins at block 602 wherein the automated dosing device 100, and specifically the central controller 200, receives a request for preparation of dosed medication delivery containers. In some embodiments, the request for preparation of dosed medication delivery containers can specify the preparation of one dosed medication delivery container, or can specify the preparation of at least one dosed medication delivery container, or in other words can specify the preparation of the plurality of dosed medication delivery containers.

At block 604 one or several attributes of the received request are determined. These attributes can include, for example, a type medication delivery containers for use in preparing the dosed medication delivery containers, a number of ingredients to be combined in the creation of the dosed medication delivery containers, a source of the ingredients to be combined in the creation of the dosed medication delivery containers, and/or a dose size for each of the ingredients to be combined in the creation of the dosed medication delivery containers. These attributes can be determined by the automated dosing device 100, and specifically by the central controller 200 of the automated dosing device 100. In some embodiments, these attributes can be determined based on information received with a request for preparation of dosed medication delivery containers.

At block 606 one or several vials and/or medication delivery containers are identified and/or inspected. In some embodiments, a user can load one or several medication delivery containers for use in creating the dosed medication delivery containers into the automated dosing device 100. This can include, for example, loading one or several syringes into the syringe carousel 118 and/or loading one or several medication bags into the back carousel 104. In some embodiments, these medication delivery containers can be inspected by the automated dosing device 100, and in some embodiments, for example, the syringes can be inspected by the syringe decap and vision module 116.

Similarly, in some embodiments, a user can load one or several vials 302 for use in creating the dosed medication delivery containers into the automated dosing device 100. These vials 302 can contain medication that can be dosed into the medication delivery containers to thereby create dosed medication delivery containers. These vials 302 can, in some embodiments, be loaded onto the vial carousel 138. The vial carousel 138 can store the vials 302, and in some embodiments can visually inspect the received vials 302. In some embodiments, this visual inspection can be performed with one or several cameras and/or scanners that can image all or portions of the vial carousel 138, and software that, when executed, analyzes image and/or video data generated by the one or several cameras and/or scanners.

In some embodiments, block 606 can include evaluation of available medication delivery containers and/or vials 302 of medication and determining if adequate medication delivery containers and/or vials 302 of medication are available for completion of the request and/or for completion of at least a desired portion the request. If it is determined that there are inadequate medication delivery containers and/or vials 302 of medication, then a request can be made to the user to provide medication delivery containers and/or vials 300 to a medication to remedy this inadequacy.

At block 608 a template corresponding to one or several attributes of the received request is identified. In some embodiments, the template can be identified by the central controller 200, and specifically can be identified by querying the memory of the central controller 200 based on the determined one or several attributes of the request. In response to this query, the memory can return the template corresponding to the one or several attributes of the request, an identifier of that template, and/or a pointer to that template. In some embodiments, this template can be retrieved from the memory as indicated in block 610 of process 600.

At optional block 611, the request is evaluated for dividing into a plurality of mini-batches. In the event that it is determined to divide the request into a plurality mini-batches, then these mini-batches are prepared. In some embodiments, the determination of whether to divide the request into the plurality mini-batches can be made based on one or several attributes of the request such as, for example, the number of dosed medication delivery devices created in completion of the request, the complexity of the creation of those dosed medication delivery devices, or the like. If the request is divided into mini-batches, the processing of each of the mini-batches can cause preparation of a subset of the plurality of dosed medication delivery containers specified in the request of block 602. In some embodiments, this evaluation and/or preparation of mini-batches, and specifically the dividing of the request into a plurality of mini-batches can be performed by the central controller 200.

After the template has been retrieved, the process 600 proceeds to block 612 wherein the retrieved template is executed. The retrieved template can be executed by the central controller 200, and specifically by the processor of the central controller 200. The template can include a plurality of steps and in order for completion of those steps, and the execution of the template by the central controller 200 can include the central controller performing those steps and/or directing stations within the automated dosing device 100 to perform those steps and/or to perform actions or operations corresponding to those steps.

In some embodiments in which the request is divided into a plurality of mini-batches, the execution of the template results in the processing of each of the mini-batches. In some embodiments, these mini-batches can be serially processed such that another mini-batch is not started until the previous mini-batch is complete.

In some embodiments, the creation of a dosed medication delivery container can result from the one time execution of the template. In other words, in some embodiments, each execution of the template can result in the creation of one dose medication delivery container. In such an embodiment, completion of a request for a plurality of dosed medication delivery containers can include executing the template a number of times. In such an embodiment, the creation of n dosed medication delivery containers can require executing the template n times.

In some embodiments, and as a part of the execution of the retrieved template, the central controller 200 can control the transport tool 102 to move vials 302 and/or medication delivery containers 502 to, from, and/or between stations of the automated dosing device 100 as indicated in block 614. In some embodiments, the robot arm 106 can be controlled to advance medication delivery containers 502 one processing step at a time by moving each medication delivery container 502 that has completed the operation of its current station to a next downstream station.

In some embodiments, the robotic arm 106 proceeds in advancing the medication delivery containers 502 according to a predetermined sequence. In some embodiments, for example, the robotic arm the first move the medication delivery container 502 that is closest to being a complete dosed medication delivery container, and decrement to then move the medication delivery container 502 that his next closest to being a complete dosed medication delivery container. This decrement in continues until all of the medication delivery containers 502 have been advanced to the next station. In some embodiments, once the robotic arm 106 has advanced the medication delivery container 502 farthest from completion, the current station of the medication delivery container 502 that is closest to being a complete dosed medication delivery container will have completed its operation, and the robotic arm 106 returns to advance this medication delivery container 502 that is closest to being a complete dose medication delivery container to its next station. The robotic arm 106 can continue to iteratively decrementally-move medication delivery containers to their next station until the requested dosed medication delivery containers are created.

Additionally, and as part of the execution of the retrieved template, the automated dosing device 100, and specifically the central controller 200 can iteratively assigned tasks to stations as indicated in block 616. In some embodiments, this can include identifying a next task in the station responsible for completion of that next task, and sending a communication to that station to launch an or perform that next task.

After completion of execution of the retrieved template, the process 600 can proceed to decision step 617, wherein it is determined if the request is completed and/or if the requested number of dosed medication delivery containers have been created. The automated dosing device 100 can monitor and/or track the number of dosed medication delivery containers, and can determine when the number of dosed medication delivery containers matches the number of dosed medication delivery containers designated for creation in the request received in block 602. When it is determined that the request is not yet completed, the process 600 returns to block 612 and again executes the retrieved template to cause the creation of another dosed medication delivery container.

Returning again to decision step 617, when it is determined that the desired number of dosed medication delivery containers have been created, then the process 600 can indicate completion of the request and/or can deliver the completed dose medication delivery containers as indicated in block 618. In some embodiments, dose medication delivery containers can be delivered by making them available for pickup and/or retrieval from the automated dosing device 100 by the user.

Figure 7:
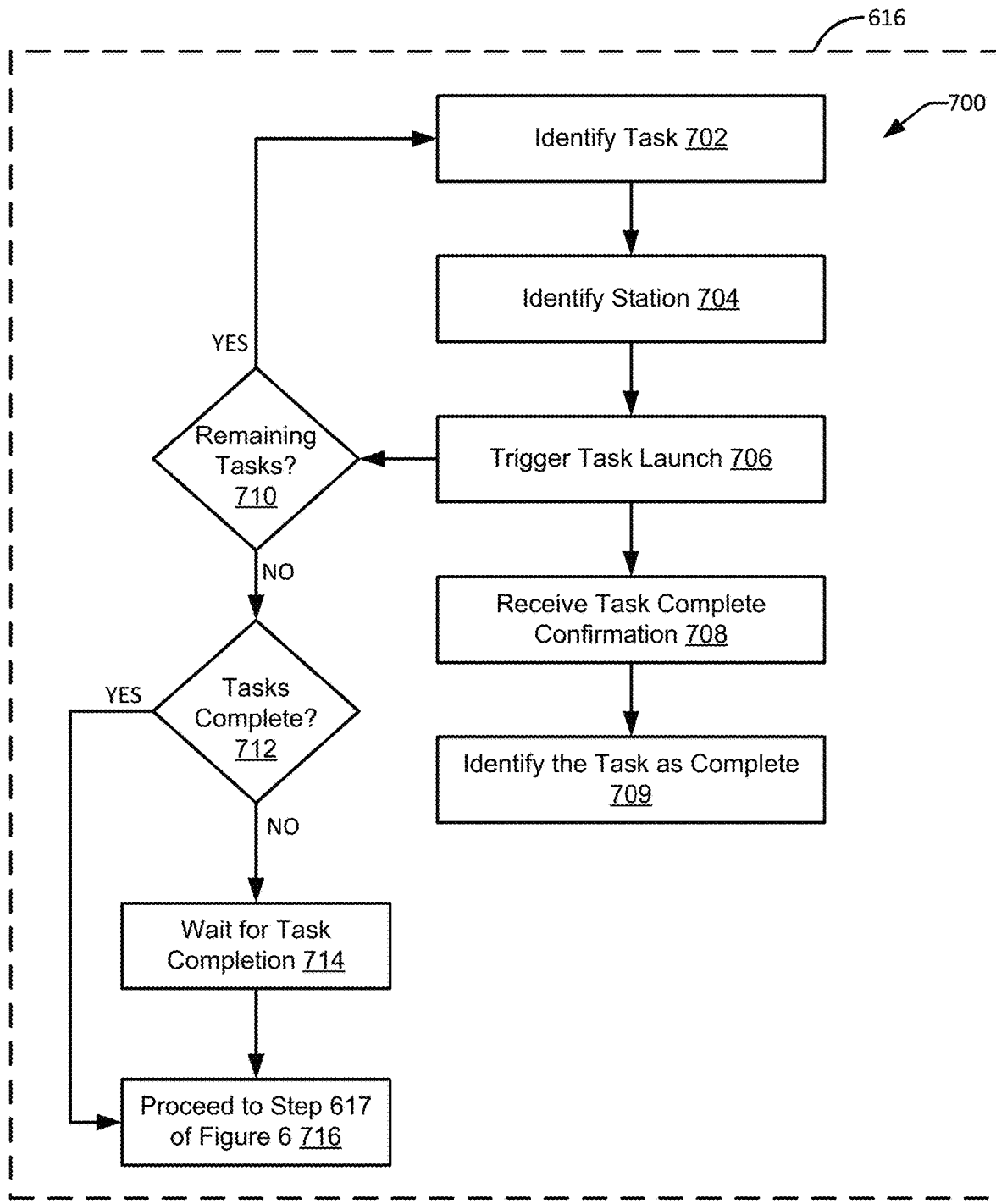
FIG. 7 is a flowchart illustrating one embodiment of a process for iteratively assigning tasks to stations within the automated dosing device.

With respect now to FIG. 7, a flowchart illustrating one embodiment of a process 700 for iteratively assigning tasks to stations within the automated dosing device 100 is shown. The process 700 can be performed by all or portions of the automated dosing device 100 including by the central controller 200. In some embodiments, the process 700 can be performed as a part of, or in the place of step of block 616 of FIG. 6.

The process 700 begins at block 702 wherein a task is identified within the template. In some embodiments, this task can be the next uncompleted task in the template, and specifically can be the next uncompleted task in the template according to the ordering of tasks in the template. This task can be identified by the central controller 200.

At block 704 a station for performing the task identified in block 702 is identified. In some embodiments, the station can be identified by the central controller 200 based on information contained in the template. In some embodiments, for example, each task in the template can include an associated station for completion of that task.

A block 706, the central controller 200 triggers launch of the task. In some embodiments, this can include generating and sending a message, which message can be an instruction, to the station identified in block 704. This message can direct the station to perform the task, and specifically can direct the station controller to control components of the station to perform the task and/or the operation associated with the task. This message can be received by the station, and specifically by the station controller, and the station controller can control components of the station to perform the task and/or operation associated with the task. In some embodiments, upon completion of the performing of that task and/or operation associated with the task, the station controller can send a message indicative of completion of performing that task and/or operation associated with the task to the central controller 200.

At block 708, the central controller 200 can receive a task completion confirmation, or in other words, can receive a message from the station controller indicating completion of the task and/or of the operation associated with the task. In some embodiments, the central controller 200 can identify that task within the template as complete as indicated in block 709.

Returning again to block 706, after triggering the task launch, the process 700 can proceed to decision step 710, wherein it is determined if there are any remaining tasks in the template. In some embodiments, the process 700 can proceed to decision step 710 while the station is performing the task and/or operation associated with the task, and/or during the performing of one or both of step 708 and step 709.

In some embodiments, the determination of decision step 710 includes determine if there are any remaining tasks in the template that are not completed or that of not the launch triggered. If it is determined that there are remaining tasks, then the process 700 can return to block 702 and proceed as outlined above.

Returning again to decision step 710, if it is determined that there are no remaining tasks, then the process 700 can proceed to decision step 712, wherein it is determined if all of the triggered tasks are complete. In some embodiments, this can include determining whether a confirmation of task completion is then received for each triggered task. If it is determined that not all tasks are complete, then the process 700 can proceed to block 714 and await completion of all triggered tasks, and thus completion of all tasks in the template. After all of the tasks in the template have been completed at block 714, or returning to decision step 712, if it is determined that all the tasks are completed, then the process 700 can continue to block 716 and can proceed to decision step 617 of FIG. 6.

Figure 8:
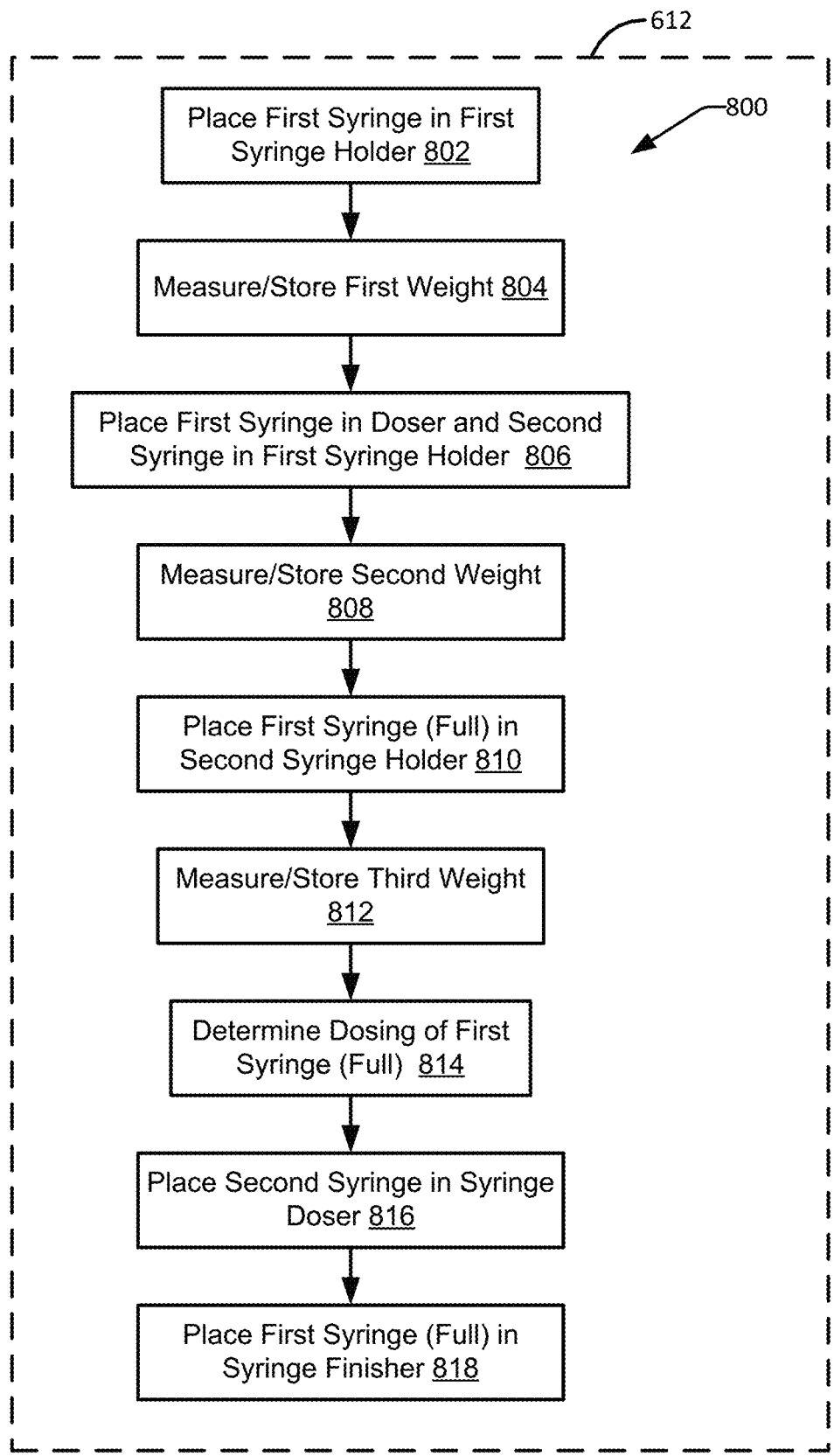
FIG. 8 is a flowchart illustrating one embodiment of a process for execution of a portion of a template.

With reference now to FIG. 8, a flowchart illustrating one embodiment of a process 800 for execution of a portion of a template is shown. The process 800 can be performed as a part of, or in the place of step 612 of FIG. 6. In some embodiments, the process 800 can be performed as a part of, or in the place of steps 614 and 616 of FIG. 6, and specifically can comprise steps as part of the performing of an operation by one station of the automated dosing device 100.

The process 800 begins at block 802, wherein a first syringe is placed in the first syringe holder 124 via the transport tool 102, and specifically via the robotic arm 106. The transport tool 102, and more specifically, the robotic arm 106 can be controlled to move the first syringe and place the first syringe in the first syringe holder 124 by, for example, the central controller 200. In some embodiments, placing the first syringe in the first syringe holder 124 can include the central controller identifying a desired syringe size for the first syringe and requesting the syringe carousel 118 to make a syringe of the desired syringe size available. In some embodiments, the syringe of the desired sizes not contained on the syringe carousel 118 or otherwise available, the automated dosing device 100 can request the user to load such a syringe into the automated dosing device 100, and specifically onto the syringe carousel 118.

In response to this request, in some embodiments, a syringe can be identified as being of the desired size. This syringe can be made available to the syringe decap and vision module 116, which can inspect a syringe to determine that it is of the requested size and that it has an exposed needle. In some embodiments, inspecting the syringe to determine that it is of the requested size can include confirming that the plunger of the syringe is at a home position and/or pushing the plunger of the syringe to the home position. When the syringe is confirmed as being of the requested size and as having an exposed needle, the syringe carousel 118 can position the syringe for pickup by the robotic arm 106. The robotic arm 106 can pick up this first syringe, which can be empty, from the syringe carousel 118 and then place the first syringe in the first syringe holder 124.

At block 804 a first weight is measured by the scale 122 and is stored. This first weight is the weight of the empty, first syringe. At block 806 the transport tool 102, and specifically the robotic arm 106 is controlled by, for example, the central controller 200 to place the first syringe in the doser 120 and to place a second syringe in the first syringe holder 124. In some embodiments, the first syringe can be filled by the doser 120 upon being placed in the doser 120.

In some embodiments, placing the second syringe in the first syringe holder 124 can include the central controller identifying a desired syringe size for the second syringe and requesting the syringe carousel 118 to make a syringe of the desired syringe size available. In response to this request, in some embodiments, a syringe can be identified as being of the desired size. This syringe can be made available to the syringe decap and vision module 116, which can inspect a syringe to determine that it is of the requested size and that it has an exposed needle. In some embodiments, inspecting the syringe to determine that it is of the requested size can include confirming that the plunger of the syringe is at a home position and/or pushing the plunger of the syringe to the home position. When the syringe is confirmed as being of the requested size and as having an exposed needle, the syringe carousel 118 can position the syringe for pickup by the robotic arm 106. The robotic arm 106 can pick up this second syringe, which can be empty, from the syringe carousel 118 and then place the second syringe in the first syringe holder 124.

At block 808, a second weight is measured by the scale 122 and is stored. The second weight is the weight of the empty, second syringe. At block 810 the now full or filled, first syringe is placed in the second syringe holder 126 via the transport tool 102, and specifically via the robotic arm 106. In some embodiments, the transport tool 102, and specifically the robotic arm 106 can be controlled by the central controller 200 to retrieve the full, first syringe from the doser 120 and to place the full, first syringe in the second syringe holder 126.

At block 812, a third weight is measured by the scale 122 and is stored. The third weight is the weight of the empty, second syringe and the full, first syringe. As both the first and second syringe holders 124, 126 are coupled to scale 122, in other words, scale 122 is common to both syringe holders 124, 126, the third weight reflects the combined weight of both the first and second syringes.

At block 814, the dosing of the full, first syringe is determined. This includes first determining a weight of the full, first syringe by determining a difference between the third weight and the second weight. Using the determined weight of the full, first syringe, the dosing of the full, first syringe can be determined by determining the difference between the weight of the full, first syringe and the first weight, which first weight is reflective of the weight of the empty, first syringe. The dosing of the full, first syringe can be determined by the central controller 200.

At block 816, the empty, second syringe is placed in the syringe doser 120 by the transport tool 102, and specifically by the robotic arm 106. In some embodiments, the transport tool 102, and specifically the robotic arm 106 I controlled by the central controller 200 to retrieve the second syringe from the first syringe holder 124 and place the second syringe in the syringe doser 120.

At block 818, if the dosed medication delivery container is a full syringe, then the full, first syringe is placed in the syringe finisher 136. Upon completion of its operations, the syringe finisher 136 can drop the completed syringe into the output bin of the automated dosing device 100. Upon completion of block 818, in some embodiments, if process 800 is performed as a part of block 612, the process 800 can proceed from block 818 to decision step 617 of FIG. 6.

Figure 9:
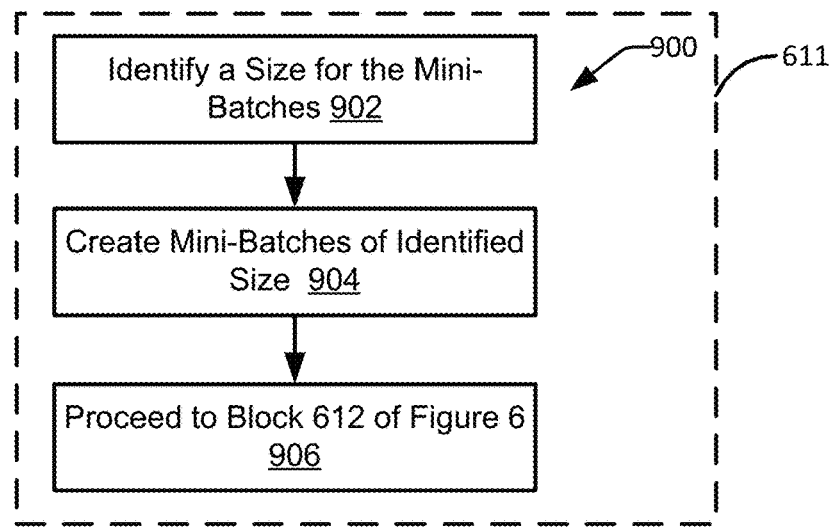
FIG. 9 is a flowchart illustrating one embodiment of a process for evaluating and/or preparing a mini-batch.

With reference now to FIG. 9, a flowchart illustrating one embodiment of a process 900 for evaluating and/or preparing a mini-batch is shown. The process 900 can be performed as a part of, or in the place of step 611 of FIG. 6. In some embodiments, the process 900 can be performed by the automated dosing device 100, and specifically by the central controller 200 of the automated dosing device 100. The process 900 begins at block 902 wherein a size for the mini-batches is identified. In some embodiments, this size for the mini-batches is identified based on one or several attributes of the request including, for example, the specified number of dosed medication delivery containers to be created in completing the request and attributes of vials 300 to a medication used in creating those dosed medication delivery containers. At block 904 a plurality of mini-batches of the identified size are created. Once these mini batches have been created, the process 900 continues to block 906 and then proceeds to block 612 of FIG. 6.

Figure 10:
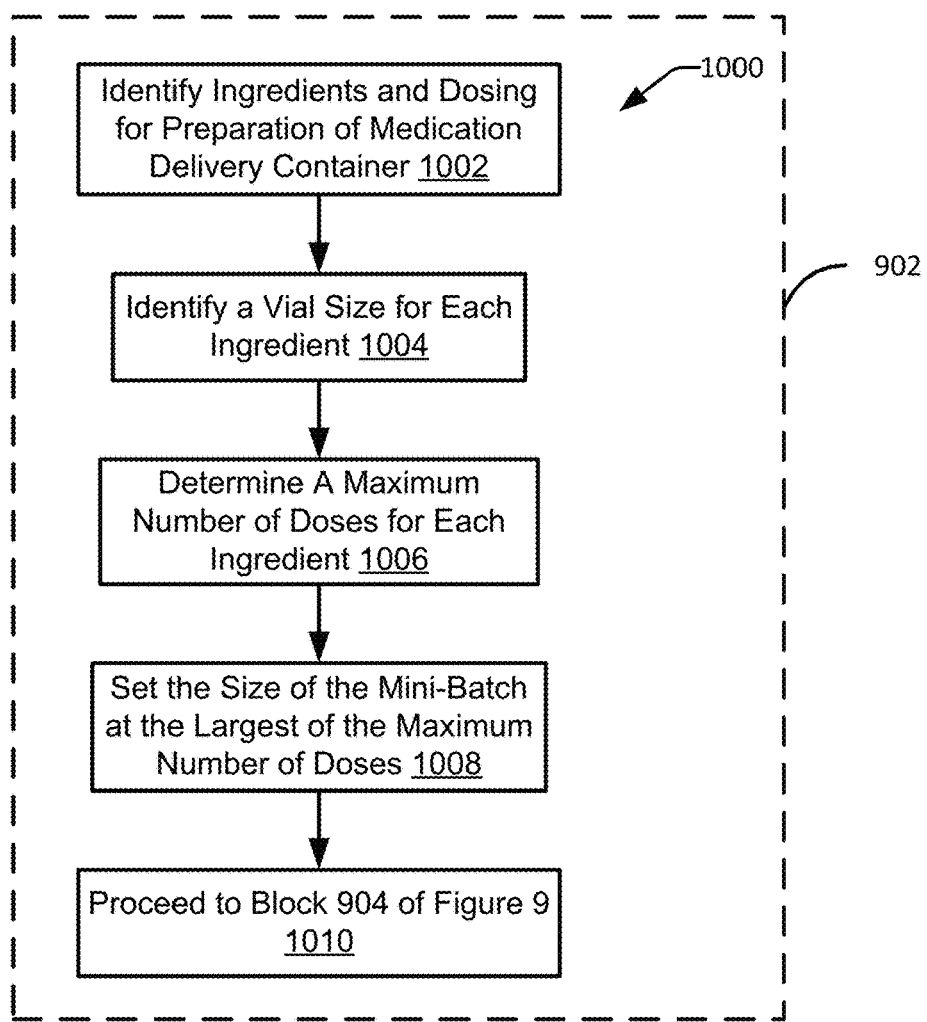
FIG. 10 is a flowchart illustrating one embodiment of a process for identifying the size for the mini-batches.

With reference now to FIG. 10, a flowchart illustrating one embodiment of a process 1000 for identifying the size for the mini-batches is shown. The process 1000 can be performed as a part of, or in the place of step of block 902 of FIG. 9. The process 1000 can be performed by the automated dosing device 100, and specifically by the central controller 200. The process 1000 begins at block 1002 wherein ingredients and dosing for preparation of dosed medication delivery containers are identified. In some embodiments, these ingredients and the dosing of those ingredients can be identified based on information received in the request a block 602 of FIG. 6.

At block 1004, a vial size for each of the ingredients used for preparation of the dosed medication delivery containers is identified. In some embodiments vial sizes can be determined as a part of step 606 of FIG. 6. In some embodiments, for example, as a vial 302 is loaded to the automated dosing device 100, the size of that file can be determined, input by a user, and/or stored in memory of or associated with the central controller 200. In some embodiments, inspection of the vial 302 can determine the size of that vial, and specifically the volume of contents of that vial 302. At block 1004, information indicative of vial sizes for each of the ingredients used for preparation of the dosed medication delivery containers can be identified. In some embodiments, this can include retrieving that information from memory of, or associated with, the central controller 200.

At block 1006 a maximum number of doses contained in the vial of each of the ingredients used in preparation of the dosed medication delivery containers is determined. In some embodiments, this maximum number of doses can be determined by dividing a vial size for an ingredient by dosing for that ingredient. The maximum number of doses can be determined by the central controller 200.

At block 1008 the size of the mini-batches can be set as a value equal to the largest of the maximum number of doses of one of the ingredients used for preparation of the dosed medication delivery containers. Once the size of the mini-batches has been set, the process 1000 continues to block 1010 and proceeds to block 904 of FIG. 9.

Figure 11:
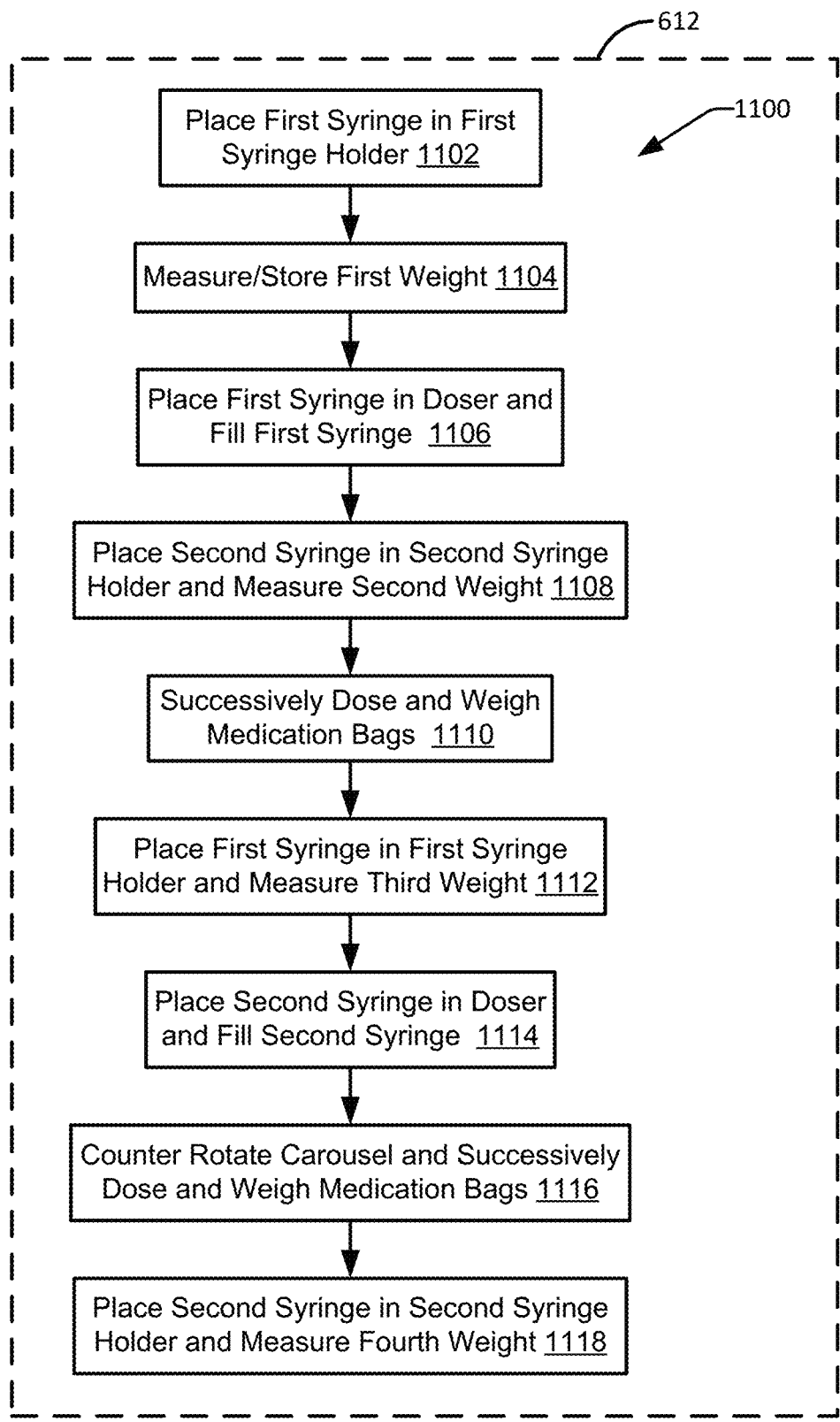
FIG. 11 is a flowchart illustrating one embodiment of a process for syringe handling during dosed medication bag creation.

With reference now to FIG. 11, a flowchart illustrating one embodiment of a process 1100 for syringe handling during dosed medication bag creation is shown. The process 1100 can be performed as a part of, or in the place of step 612 of FIG. 6. In some embodiments, the process 1100 can be performed as a part of, or in the place of steps 614 and 616 of FIG. 6, and specifically can comprise steps as part of the performing of an operation by one station of the automated dosing device 100.

The process 1100 begins at block 1102, wherein a first syringe is placed in the first syringe holder 124 of the scale 122. In some embodiments the central controller 200 can control the transport tool 102, and specifically the robotic arm 106 to retrieve the first syringe from, for example, the syringe carousel 118 and to place the first syringe in the first syringe holder 124. At block 1104, a first weight is measured and stored by the scale 122. This first weight can be the weight of the empty first syringe. This first weight can be stored by the scale 122, and specifically by the station controller of the scale 122.

At block 1106, the first syringe is placed in the doser 120 and is filled by the doser 120. In some embodiments, the central controller 200 can control the transport tool 102, and specifically the robotic arm 106 to retrieve the first syringe from the first syringe holder 124 and place the first syringe in the doser 120. In some embodiments, the first syringe can be secured in the doser 120 by one or several features of the doser 120 such as, for example, by one or several gripping and/or clamping features.

In some embodiments, and as a part of filling the first syringe, the central controller can identify a vial 302 containing medication, and specifically a first medication, for using in filling the first syringe. If this identified vial contains a powdered medication or other medication meeting reconstitution, the transport tool 102, and specifically the robotic arm 106 can be controlled by the central controller 200 to transport the vial 302 to the reconstitution module 130, which reconstitution module 130 can inject a diluent into the vial 302. The transport tool 102, and specifically the robotic arm 106 can be controlled by the central controller 200 to transport the vial 302 from the reconstitution module 130 to a reconstitution mixer 132. The vial 302 can be agitated by the reconstitution mixer 132 to dissolve the powdered medication in the diluent. Upon the successful dissolution of the powdered first medication into the diluent, the transport tool 102, and specifically the robotic arm 106 can be controlled by the central controller 200 to transport the vial from the reconstitution mixer 132 to the scale 122 to be weighed. This weight of the full vial 302 can be stored, and then the transport tool 102, and specifically the robotic arm 106 can be controlled by the central controller to transport the vial 302 to the doser 120. The doser 120 can retain that vial 302, and can fill the first syringe from vial 302.

If the filling of the first syringe empties the vial 302, then the vial 302 is transported by the transport tool 102, and specifically by the robotic arm 106 to the scale 122. The weight of the empty vial 302 is measured by the scale 122 to determine if the vial 302 is sufficiently empty. If the vial 302 is sufficiently empty, then the vial 302 can be disposed. In some embodiments, if further medication for filling the first syringe is desired, then one or several additional vials 302 containing this medication can be prepared and transported to the doser 120 in the same manner as discussed above.

At block 1108 a second syringe is placed in the second syringe holder 126 of the scale 122. In some embodiments the central controller 200 can control the transport tool 102, and specifically the robotic arm 106 to retrieve the second syringe from, for example, the syringe carousel 118 and to place the second syringe in the second syringe holder 126.

At block 1110, medication bags are successively dosed and weighed. In some embodiments, the medication bags can be dosed by the doser 120 and can be weighed by the scale 122. The dosing and weighing of a medication bag can include the rotation of the bag carousel 104 to a desired position and the transport of the medication bag from the bag carousel 104 to the doser 120 via the bag shuttle 114. In some embodiments, the medication bag can be directly transferred from the bag carousel 104 to the doser 120, and in some embodiments, the medication bag can be indirectly transferred from the bag carousel 104 to the doser 120 via an intermediate transfer to the scale 122. The scale 122 can measure a first bag weight of the medication bag before the injection of a dose of medication into the medication bag by the doser 120. In such embodiments, the medication bag can be transferred from the scale 122 to the doser 120 after the measuring of the first bag weight of the medication bag. The doser 120 can inject a dose of medication into the medication bag from/with the first syringe, which dose can be of a predetermined and/or desired size.

The medication bag can be transferred from the doser 120 back to the bag carousel 104. In some embodiments, the medication bag can be directly transferred from the doser 122 the bag carousel 104, and in some embodiments, the medication bag can be indirectly transferred from the doser 120 to the bag carousel 104 via an intermediate transfer to the scale 122 for weighing of the medication bag and then a transfer from the scale 122 to the bag carousel 104.

In some embodiments, weighing the medication bags on the scale 122 can include placing a medication bag on the scale 122 and measuring the weight of the medication bag, and specifically measuring a second bag weight of the medication bag after the injecting of a dose of the medication into the medication bag by the doser 120. In some embodiments, one or several syringes may be held in the syringe holders 124, 126 of the scale 122, and measuring the weight of the medication bag can include measuring the weight of the medication bag and of a least one syringe in the scale 122. From this measured weight, the weight of the medication bag can be determined. In some embodiments, this weight of the medication bag can be determined based on a plurality of weights of multiple medication delivery containers measured by the scale 122, which multiple medication delivery containers can include the medication bag and a syringe.

In some embodiments, a dosing of the medication bag can be determined. This dosing can be determined based on the first and second bag weights. Specifically, in some embodiments, this dosing can be determined by determining the difference between the second bag weight and the first bag weight, which difference corresponds to the amount of medication injected into the medication bag by the doser 120. In embodiments in which the first bag weight and/or the second bag weight includes the weight of one or several syringes, the weight of those syringes can be removed from the measured first bag weight and/or the measured second bag weight by subtracting a previously determined weight(s) of those one or several syringes from the affected first and/or second bag weights.

After the dosed medication bag has been returned to the bag carousel 104, the bag carousel 104 can rotate in a first direction to position a next medication bag for transferring to the doser 120 for dosing. The above outlined filling and weighing process can be repeated for this next medication bag, and for further next medication bags until a desired number of medication bags have been dosed with the first medication and weighed. In some embodiments this desired number of medication bags can be set by the size of the request and/or by the size of the mini-batch.

Upon completion of the step of block 1110, the process 1100 proceeds to block 1112 wherein the first syringe is removed from the doser 120 and placed in the first syringe holder 124 of the scale 122. In some embodiments, the transport tool 102, and specifically the robotic arm 106 can be controlled by the central controller 200 to remove the first syringe from the doser 120 and place the first syringe in the first syringe holder 124. The scale 122 can measure a third weight, which third weight can include the weight of the first syringe. With this third weight, the second weight, and the first weight, any amount of residual medication in the first syringe can be determined.

In some embodiments, if the first syringe will not be reused and, after determining the residual amount of medication the first syringe, if that amount of residual medication is an acceptable amount, the first syringe can be disposed of. Alternatively, if the first syringe will be reused such as for delivering doses of the first medication to further medication bags such as in further mini-batches, the first syringe can be left in the first syringe holder 124, or if more than two syringes are used in the creation of a dosed medication delivery container, the first syringe can be returned to the syringe carousel 118 to free the first syringe holder 124 for receipt of further syringes such as, for example, a third syringe.

At block 1114, the second syringe is removed from the second syringe holder 126, placed in the doser 120 and filled. In some embodiments, the central controller 200 can control the transport tool 102, and specifically the robotic arm 106 to retrieve the second syringe from the second syringe holder 126 and place the second syringe in the doser 120. In some embodiments, the second syringe can be secured in the doser 120 by one or several features of the doser 120 such as, for example, by one or several gripping and/or clamping features.

In some embodiments, and as a part of filling the second syringe, the central controller 200 can identify a vial 302 containing medication, and specifically a second medication, for using in filling the second syringe. If this identified vial contains a powdered medication or other medication meeting reconstitution, the transport tool 102, and specifically the robotic arm 106 can be controlled by the central controller 200 to transport the vial 302 to the reconstitution module 130, which reconstitution module 130 can inject a diluent into the vial 302. The transport tool 102, and specifically the robotic arm 106 can be controlled by the central controller 200 to transport the vial 302 from the reconstitution module 130 to the reconstitution mixer 132. The vial 302 can be agitated by the reconstitution mixer 132 to dissolve the powdered medication in the diluent. Upon the successful dissolution of the powdered second medication into the diluent, the transport tool 102, and specifically the robotic arm 106 can be controlled by the central controller 200 to transport the vial 302 from the reconstitution mixer 132 to the scale 122 to be weighed. This weight of the full vial 302 can be stored, and then the transport tool 102, and specifically the robotic arm 106 can be controlled by the central controller 200 to transport the vial 302 to the doser 120. The doser 120 can retain that vial 302, and can fill the second syringe from vial 302.

If the filling of the second syringe empties the vial 302, then the vial 302 can be transported by the transport tool 102, and specifically by the robotic arm 106 to the scale 122. The weight of the empty vial 302 can be measured by the scale 122 to determine if the vial 302 is sufficiently empty. If the vial 302 is sufficiently empty, then the vial 302 can be disposed. In some embodiments, if further medication for filling the second syringe is desired, then one or several additional vials 302 containing this second medication can be prepared and transported to the doser 120 in the same manner as discussed above.

At block 1116, medication bags are successively dosed with the second medication and weighed. In some embodiments, the medication bags can be dosed by the doser 120 and can be weighed by the scale 122. The dosing and weighing of a medication bag can include the rotation of the bag carousel 104 to a desired position and the transport of the medication bag from the bag carousel 104 to the doser 120 via the bag shuttle 114. This rotation can be in the opposite direction of the rotation of the bag carousel 104 in block 1110. Through this rotation in block 1110 and counter rotation in block 1116, the automated dosing device 100 can efficiently dose medication bags such that in the first dosing pass of block 1110 the medication bags are dosed in incrementing order (e.g., 1, 2, 3, 4, 5, 6, . . . ) and in the second dosing pass of block 1116 the medication bags are dosed in decrementing order (e.g., . . . , 6, 5, 4, 3, 2, 1).

In some embodiments, the medication bag can be directly transferred from the bag carousel 104 to the doser 120, and in some embodiments, the medication bag can be indirectly transferred from the bag carousel 104 to the doser 120 via an intermediate transfer to the scale 122. The scale 122 can measure a third bag weight of the medication bag before the injection of a dose of medication into the medication bag by the doser 120. In such embodiments, the medication bag can be transferred from the scale 122 to the doser 120 after the measuring of the third bag weight of the medication bag. The doser 120 can inject a dose of the second medication into the medication bag from/with the second syringe, which dose can be of a predetermined and/or desired size.

The medication bag can be transferred from the doser 120 back to the bag carousel 104. In some embodiments, the medication bag can be directly transferred from the doser 122 the bag carousel 104, and in some embodiments, the medication bag can be indirectly transferred from the doser 120 to the bag carousel 104 via an intermediate transfer to the scale 122 for weighing of the medication bag and then a transfer from the scale 122 to the bag carousel 104.

In some embodiments, this weighing the medication bags on the scale 122 can include placing the medication bag on the scale 122 and measuring the weight of the medication bag, and specifically measuring a fourth bag weight of the medication bag after the injecting of a dose of the second medication into the medication bag by the doser 120. In some embodiments, one or several syringes may be held in the syringe holders 124, 126 of the scale 122, and measuring the weight of the medication bag can include measuring the weight of the medication bag and of a least one syringe in the scale 122. From this measured weight, the weight of the medication bag can be determined. In some embodiments, this weight of the medication bag can be determined based on a plurality of weights of multiple medication delivery containers measured by the scale 122, which multiple medication delivery containers can include the medication bag and a syringe.

In some embodiments, a dosing of the medication bag can be determined. This dosing can be determined based on the third and fourth bag weights. Specifically, in some embodiments, this dosing can be determined by determining the difference between the fourth bag weight and the third bag weight, which difference corresponds to the amount of medication injected into the medication bag by the doser 120. In embodiments in which the third bag weight and/or the fourth bag weight includes the weight of one or several syringes, the weight of those syringes can be removed from the measured third bag weight and/or the measured fourth bag weight by subtracting previously determined weight(s) of those one or several syringes from the affected third and/or fourth bag weights.

After the dosed medication bag has been returned to the bag carousel 104, the bag carousel 104 can counter rotate, or in other words, rotate in a second direction opposite to the first direction, to position a next medication bag for transferring to the doser 120 for dosing. The above outlined filling and weighing process can be repeated for this next medication bag, and for further next medication bags until a desired number of medication bags have been dosed with the second medication and weighed. In some embodiments this desired number of medication bags can be set by the size of the request and/or by the size of the mini-batch.

Upon completion of the step of block 1116, the process 1100 proceeds to block 1118 wherein the second syringe is removed from the doser 120 and placed in the second syringe holder 126 of the scale 122. In some embodiments, the transport tool 102, and specifically the robotic arm 106 can be controlled by the central controller 200 to remove the second syringe from the doser 120 and place the second syringe in the second syringe holder 126. The scale 122 can measure a fourth weight, which fourth weight can include the weight of the second syringe. With this fourth weight and the second weight, any amount of residual medication in the second syringe can be determined. In some embodiments, upon completion of block 1118, and if process 1100 is performed as a part of block 612, the process 1100 can proceed from block 1118 to decision step 617 of FIG. 6.

In some embodiments, if the second syringe will not be reused and, after determining the residual amount of medication the first syringe, if that amount of residual medication is an acceptable amount, the second syringe can be disposed of. Alternatively, if the second syringe will be reused such as for delivering doses of the second medication to further medication bags such as in further mini-batches, the second syringe can be left in the second syringe holder 126, or if more than three syringes are used in the creation of the dosed medication delivery container, the second syringe can be returned to the syringe carousel 118 to free the second syringe holder 126 for receipt of further syringes such as, for example, a fourth syringe. In the event that third, fourth, or further syringes are used to provide further doses of medication in the creation of the dosed medication delivery containers, process 1100 can be repeated for those further syringes.

Figure 13:
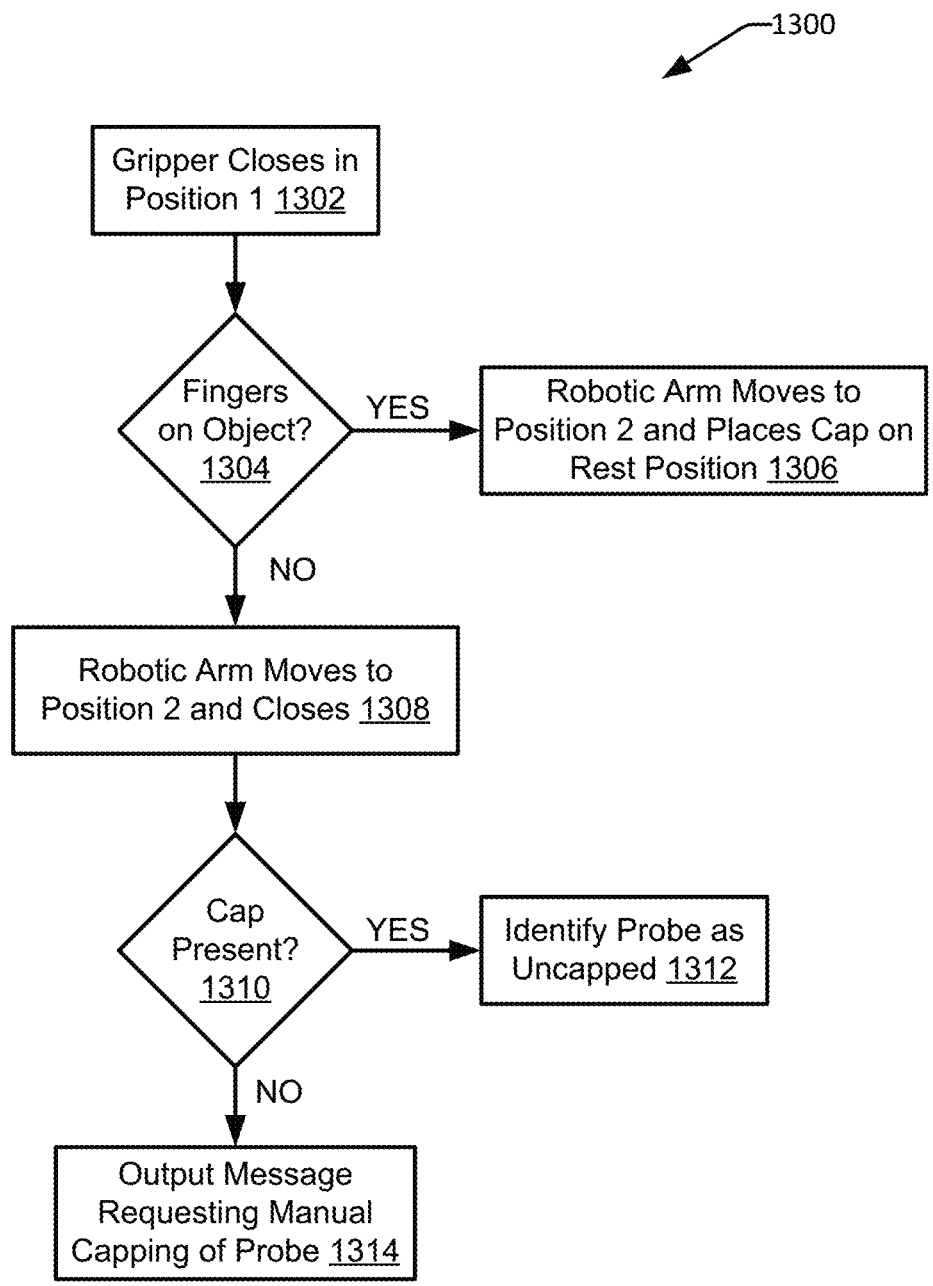
FIG. 13 is a flowchart illustrating one embodiment of a process for uncapping the inlet of a probe and for moving the cap to the cap rest.

With reference now to FIG. 13, a flowchart illustrating one embodiment of a process 1300 for uncapping the inlet 1200, and for moving the cap 1204 to the cap holder 1206 is shown. The process 1300 can be performed by the robotic arm 106, which can be controlled by the central controller 200. The process begins at block 1302 wherein the robotic arm 106 moves to position 1, which position is proximate to the inlet 1200 of the probe 146. Once at position 1, the robotic arm 106 can close its gripper. At decision step 1304, it is determined if the gripper fingers are on an object, or more specifically are on the cap 1204. In some embodiments, the robotic arm 106 and/or the central controller 200 assumes that any object gripped by the robotic arm 106 at position 1 is the cap 1204.

If the gripper of the robotic arm 106 grips the cap 1204, then the process 1300 proceeds to block 1306 and the robotic arm 106 moves to position 2, which position is proximate to the cap rest 1206. The robotic arm 106 then places the cap 1204 on the cap rest 1206. Returning again to decision step 1304, if it is to determined that the gripper fingers are not on an object, than the process 1300 proceeds to block 1308 wherein the robotic arm 106 moves to position 2 and the gripper closes. At decision step 1310 it is determined if the cap 1204 is present at position 2. In some embodiments, if the cap 1204 was not found at position 1, any object gripped by the robotic arm 106 at position 2 is assumed to be the cap 1204.

If it is determined that the cap 1204 is present at position 2, then the process 1300 proceeds to block 1312 and the probe 1200 is identified as uncapped. Returning again to decision step 1310, if it is determined that the cap 1204 is not present at position 2, then the process 1300 proceeds to block 1314 and outputs a message requesting manual capping of the probe, which manual capping can, in some embodiments, be performed the next time the automated dosing device 100 is opened.

Figure 14:
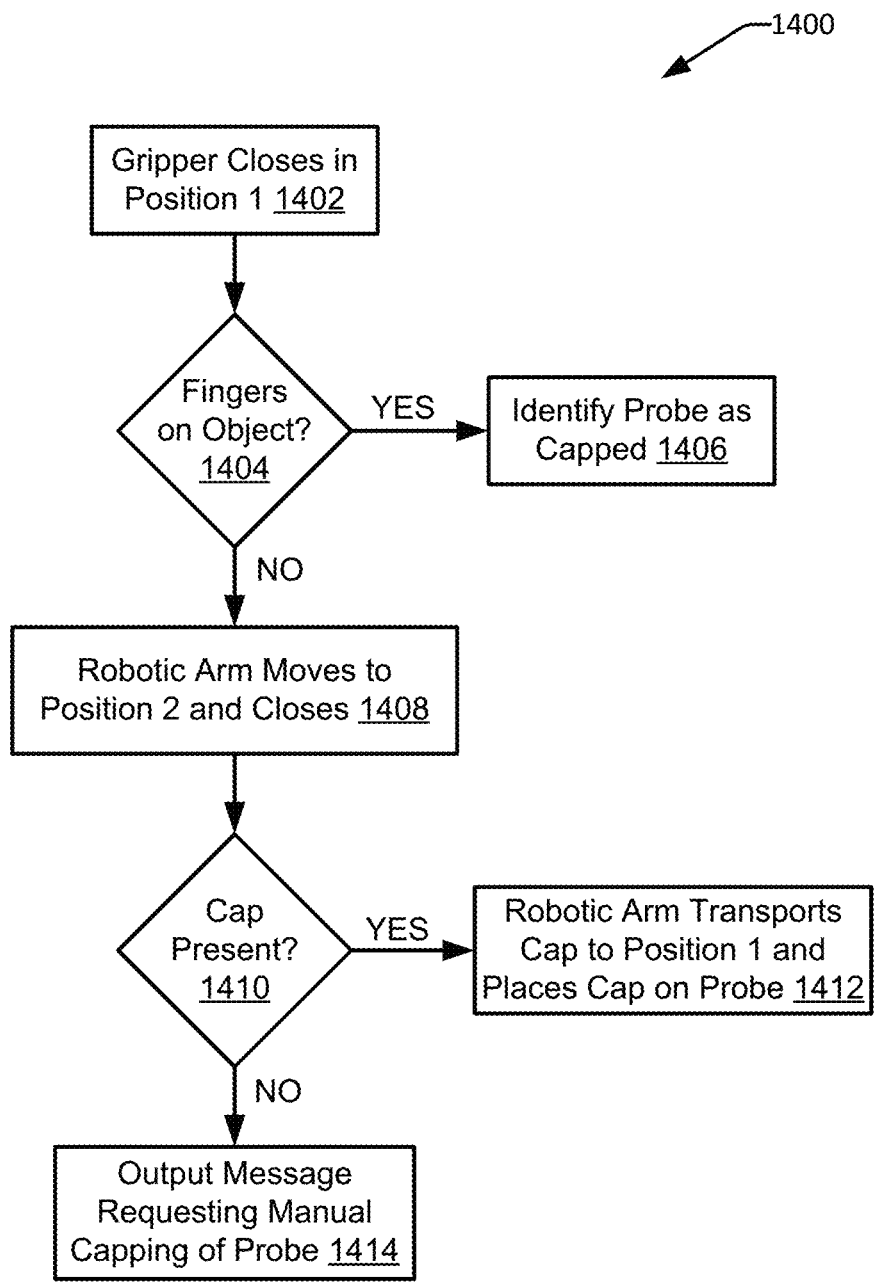
FIG. 14 is a flowchart illustrating one embodiment of a process for capping an inlet of the probe.

With reference now to FIG. 14, a flowchart illustrating one embodiment of a process 1400 for capping an inlet 1200 of the probe 146 is shown. The process can be performed by the robotic arm 106, which can be controlled by the central controller 200. The process 1400 begins at block 1402 wherein the robotic arm 106 moves to position 1, which position is proximate to the inlet 1200 of the probe 146. Once at position 1, the robotic arm 106 can close its gripper. At decision step 1404, it is determined if the gripper fingers of the robotic arm 106 are on an object, or more specifically are on the cap 1204. In some embodiments, the robotic arm 106 and/or the central controller 200 assume that any object gripped by the robotic arm 106 at position 1 is the cap 1204.

If the gripper of the robotic arm 106 grips the cap 1204, then the process 1400 proceeds to block 1406 wherein the probe 146 is identified as capped. Returning again to decision step 1404 if it is to determined that the gripper fingers are not on an object, than the process 1400 proceeds to block 1408 wherein the robotic arm 106 moves to position 2 and the gripper closes.

At decision step 1410 it is determined if the cap 1204 is present at the position 2. In some embodiments, if the cap 1204 was not found at position 1, any object gripped by the robotic arm 106 at position 2 is assumed to be the cap 1204. If it is determined that the cap 1204 is present, then the process 1400 proceeds to block 1412, wherein the robotic arm 106 moves to position 1 and places the cap 1204 on the probe 146.

Returning again to decision step 1410, if it is determined that the cap 1204 is not present at position 2, then the process 1400 proceeds to block 1414 and outputs a message requesting manual capping of the probe, which manual capping can, in some embodiments, be performed the next time the automated dosing device 100 is opened.

Figure 15:
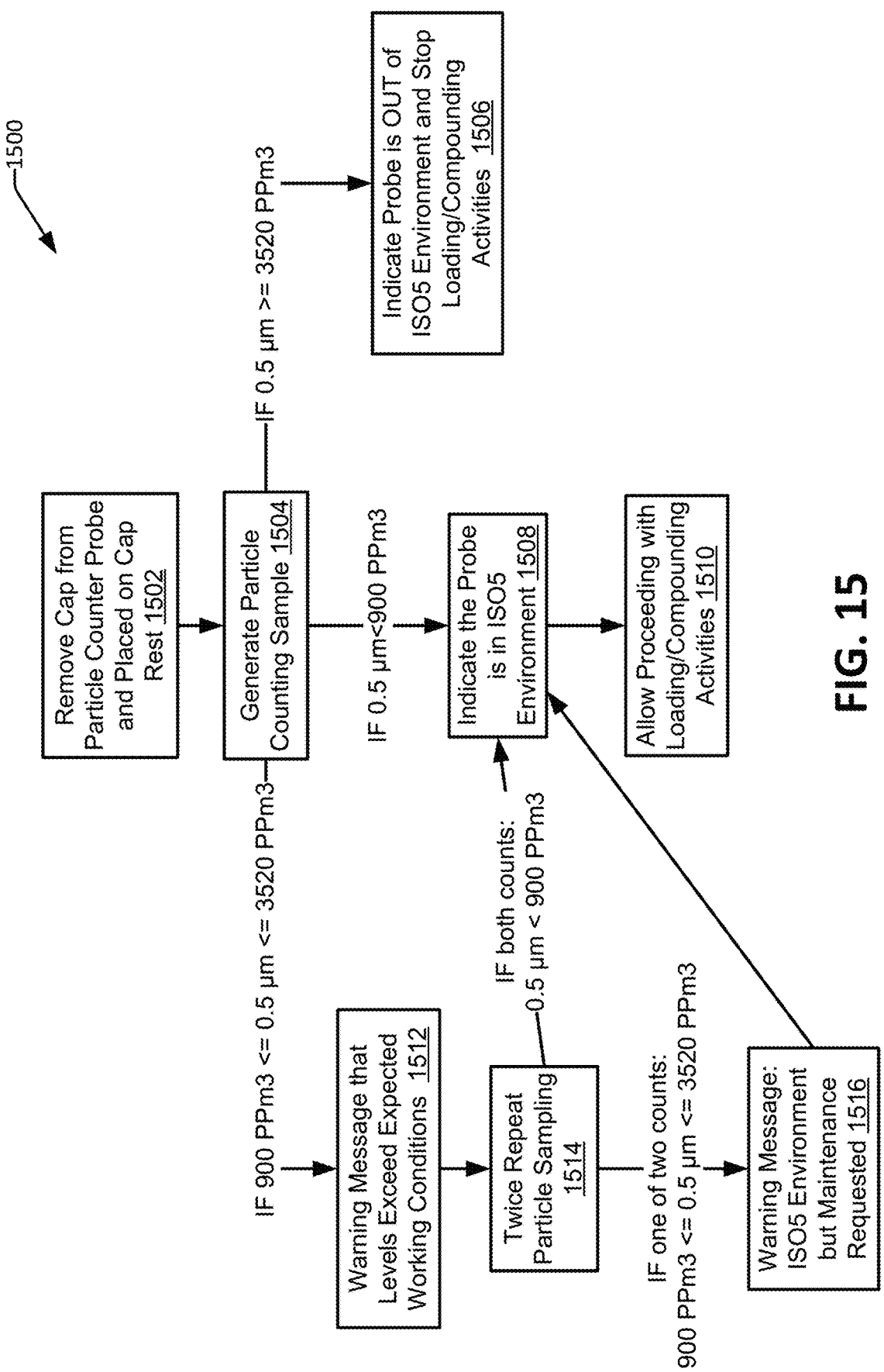
FIG. 15 is a flowchart illustrating one embodiment of a process for performing a quality check.

With reference now to FIG. 15, a flowchart illustrating one embodiment of a process 1500 for performing a quality check is shown. In some embodiments, the quality check process 1500 can be performed each time the automated dosing device 100 is initialized. The quality check process 1500 can test the quality of air in the DCA 142. The quality check process 1500 can be performed by, for example, the robotic arm 106, the probe 146, and/or the particle counter sensor unit 148. The process 1500 begins at block 1502 wherein the cap 1204 is removed from the inlet 1200 of the probe 146 by the robotic arm 106 and is placed on the cap rest 1206.

At block 1504, a particle counting sample is collected by the probe 146 and passed to the particle counter sensor unit 148. In some embodiments, this sample can be collected for two minutes, and can be collected before allowing any loading and/or compounding activity on the automated dosing device 100. The particle counter sensor unit 148 can analyze the air sample and can determine the amount of contaminants and/or particulate in the air sample. If it is determined that the number of particulates having a size greater than or equal to 0.5 μm is greater than or equal to 3520 PPm3, then the process 1500 proceeds to block 1506 and an indication that the probe 146 is in an environment outside of a desired standard, such as ISO 14644-1:2015, class 5, is provided. In some embodiments, this can further include stopping loading and/or compounding activities of the automated dosing device 100.

Returning again to step 1504, if it is determined that the number of particulates having a size greater than or equal to 0.5 μm is less than 900 PPm3, then the process 1500 proceeds to block 1508 and indicates that the probe 146 is in an environment complying with a desired standard, such as ISO 14644-1:2015, class 5, is provided. In some embodiments, this can further include allowing the automated dosing device 100 to proceed with loading and/or compounding activities.

Returning again to step 1504, if it is determined that the number of particulates having a size greater than or equal to 0.5 μm is greater than or equal to 900 PPm3 and less than or equal to 3520 PPm3, then the process 1500 proceeds to block 1512 and a warning message is generated. This warning message can indicate that the probe 146 is in an environment complying with a desired standard, such as ISO 14644-1:2015, class 5, but that the particulate levels sampled by the probe 146 are greater than expected.

The process 1500 can then proceed to block 1514, wherein two additional consecutive one minute samplings of air are collected and evaluated. If it is determined that both air samples have a number of particulates with a size greater than or equal to 0.5 μm that is less than 900 PPm3, then the process proceeds to block 1508 and proceeds as outlined above.

If it is determined that at least one of the two additional consecutive one minute samplings of air has a number of particulates with a size greater than or equal to 0.5 μm that is greater than or equal to 900 PPm3 and less than or equal to 3520 PPm3, then the process 1500 proceeds to block 1516 and a warning message is generated. This warning message indicates that the probe 146 is in an environment complying with a desired standard such as ISO 14644-1:2015, class 5, but that preventative maintenance is desired and/or should be requested.

Figure 16:
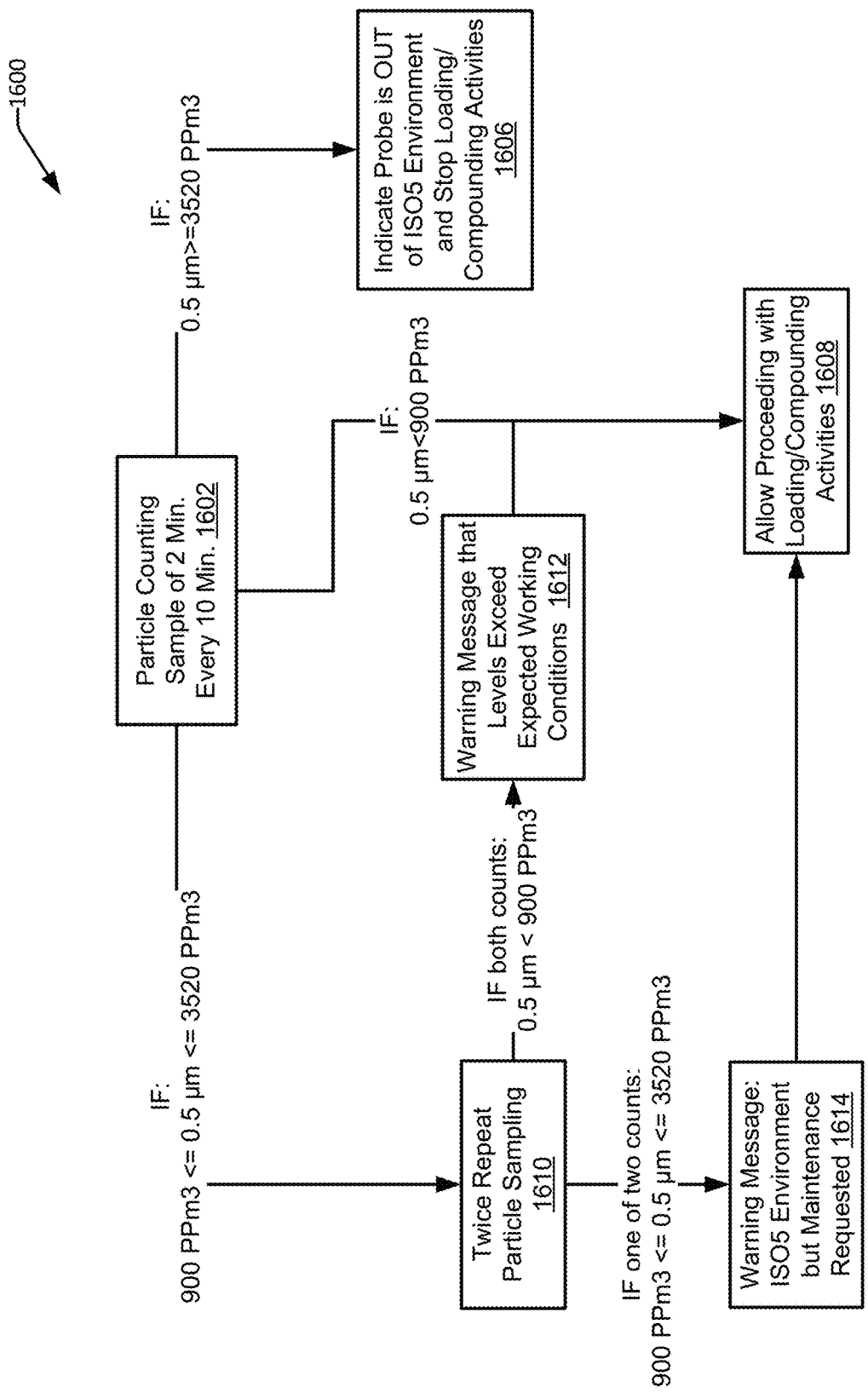
FIG. 16 is a flowchart illustrating one embodiment of a process for continuous quality monitoring.

With reference now to FIG. 16, a flowchart illustrating one embodiment of a process 1600 for continuous quality monitoring is shown. In such an embodiment, the probe 146 can remain decapped for the entire compounding process to allow for continuous particle monitoring. In such an embodiment, the particle counter sensor unit 148 can provide continuous feedback to the automated dosing device 100 about air quality inside of the DCA 142. Based on a comparison of measured particle levels to one or several one or several thresholds, alerts and/or stop a trigger to inform the user of air quality within the DCA 142 and/or to stop the operation of the automated dosing device 100. The process 1600 begins at block 1602 wherein a particle collecting sample having a duration of two minutes is collected once every 10 minutes. This sample can be collected by the probe 146 and can be processed by the particle counters sensor unit 148.

If it is determined that the number of particulates having a size greater than or equal to 0.5 μm is greater than or equal to 3520 PPm3, then the process 1600 proceeds to block 1606 and an indication that the probe 146 is in an environment outside of a desired standard, such as ISO 14644-1:2015, class 5, is provided. In some embodiments, this can further include stopping loading and/or compounding activities of the automated dosing device 100.

Returning again to block 1602, if it is determined that the number of particulates having a size greater than or equal to 0.5 μm is less than 900 PPm3, then the process 1600 proceeds to block 1508 and allows the automated dosing device 100 to proceed with loading and/or compounding activities.

Returning again to block 1602, if it is determined that the number of particulates having a size greater than or equal to 0.5 μm is greater than or equal to 900 PPm3 and less than or equal to 3520 PPm3, then the process 1600 proceeds to block 1610, wherein two additional consecutive one minute samplings of air are collected and evaluated. If it is determined that both air samples have a number of particulates with a size greater than or equal to 0.5 μm that is less than 900 PPm3, then the process 1600 proceeds to block 1612 and a warning message is generated. This warning message can indicate the measured particulate levels exceeded expected working conditions, or more specifically that the probe is in an environment outside of a desired standard, such as ISO 14644-1:2015, class 5, but that one sample has exceeded the expected working conditions. The process 1600 can then continue to block 1608 and can proceed as outlined above.

Returning again to block 1610, if it is determined that at least one of the two additional consecutive one minute samplings of air has a number of particulates with a size greater than or equal to 0.5 µm that is greater than or equal to 900 PPm3 and less than or equal to 3520 PPm3, then the process 1600 proceeds to block 1614 and a warning message is generated. This warning message indicates that the probe 146 is in an environment complying with a desired standard such as ISO 14644-1:2015, class 5, but that preventative maintenance is desired and/or should be requested. The process 1600 can then continue to block 1608 and can proceed as outlined above.

Figure 17:
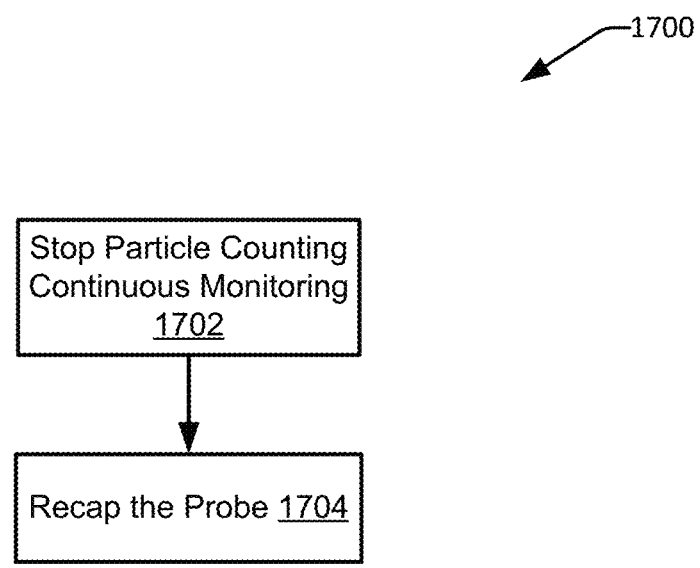
FIG. 17 is a flowchart illustrating one embodiment of a process for shutdown of the automatic dosing device.

With reference now to FIG. 17, a flowchart illustrating one embodiment of a process 1700 for shutdown of the automatic dosing device 100 is shown. The process 1700 can be performed in connection with the process 1600 of FIG. 16, and specifically the process 1700 relates to the shutting down of continuous monitoring as outlined in the process 1600 of FIG. 16. In some embodiments, process 1700 can be performed prior to shut down of the automatic dosing device 100 such as, for example, shutdown for opening of the automatic dosing device 100 and/or cleaning of the automatic dosing device 100.

The process 1700 begins at block 1702 wherein the process 1600 of FIG. 16 is terminated, or in other words, continuous particulate monitoring is terminated. The process 1700 then proceeds to block 1704 wherein probe 146 is recapped. This can be performed by, for example, the robotic arm 106 which can retrieve the cap 1204 from the cap rest 1206 and place the cap 1204 on the inlet 1200 of the probe 146.

Figure 18:
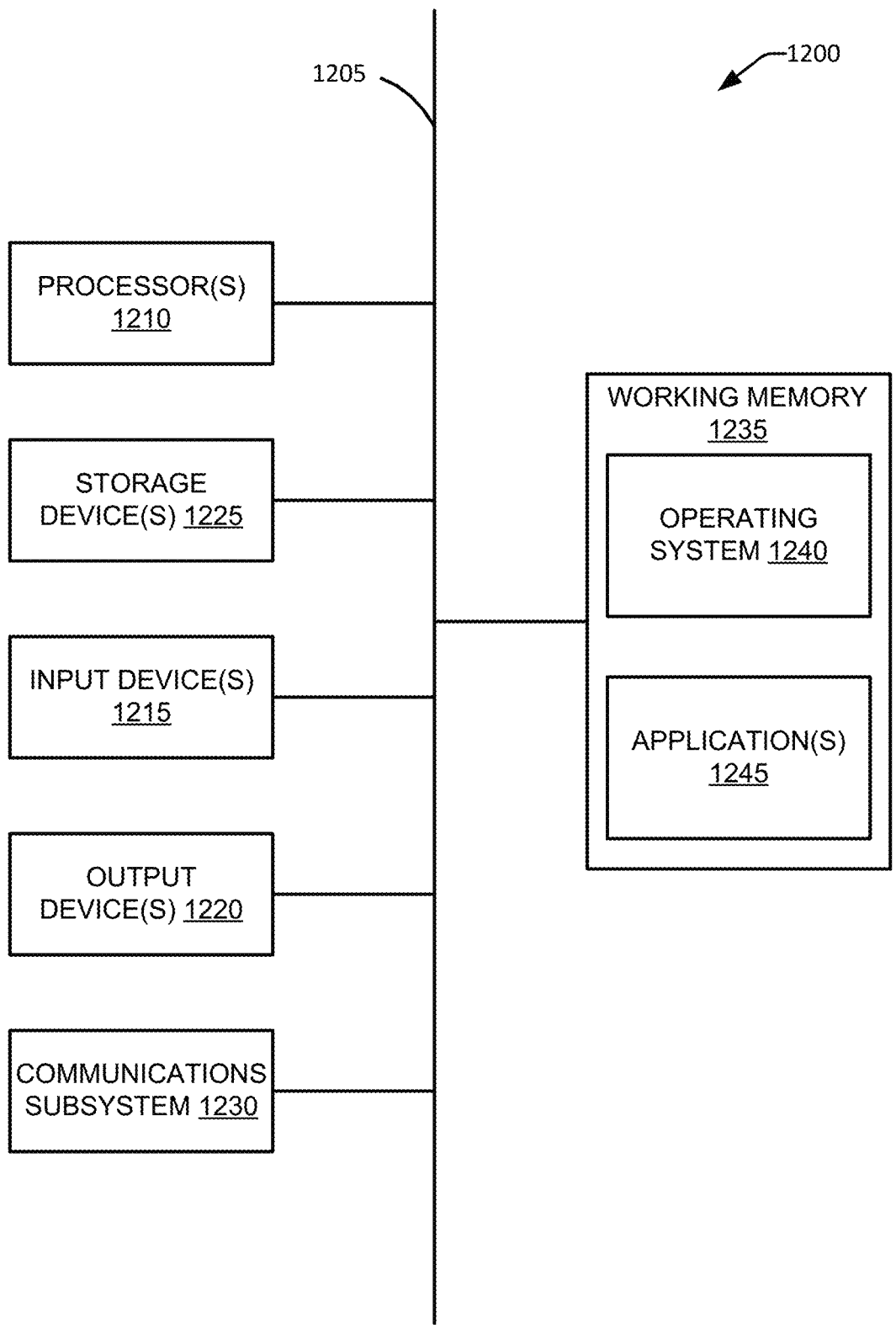
FIG. 18 is a schematic illustration of on embodiment of a computer system.

With reference now to FIG. 18, a computer system may be incorporated as part of the previously described computerized devices. For example, computer system 1200 can represent some of the components of automated dosing device 100, central controller 200, station controllers, and/or other computing devices described herein. FIG. 12 provides a schematic illustration of one embodiment of a computer system 1200 that can perform the methods provided by various other embodiments, as described herein. FIG. 12 is meant only to provide a generalized illustration of various components, any or all of which may be utilized as appropriate. FIG. 12, therefore, broadly illustrates how individual system elements may be implemented in a relatively separated or relatively more integrated manner.

The computer system 1200 is shown comprising hardware elements that can be electrically coupled via a bus 1205 (or may otherwise be in communication, as appropriate). The hardware elements may include a processing unit 1210, including without limitation one or more processors, such as one or more special-purpose processors (such as digital signal processing chips, graphics acceleration processors, and/or the like); one or more input devices 1215, which can include without limitation a keyboard, a touchscreen, receiver, a motion sensor, an imaging device, and/or the like; and one or more output devices 1220, which can include without limitation a display device, a speaker, and/or the like.

The computer system 1200 may further include (and/or be in communication with) one or more non-transitory storage devices 1225, which can comprise, without limitation, local and/or network accessible storage, and/or can include, without limitation, a disk drive, a drive array, an optical storage device, a solid-state storage device such as a random access memory ("RAM") and/or a read-only memory ("ROM"), which can be programmable, flash-updateable and/or the like. Such storage devices may be configured to implement any appropriate data stores, including without limitation, various file systems, database structures, and/or the like.

The computer system 1200 might also include a communication interface 1230, which can include without limitation a modem, a network card (wireless or wired), an infrared communication device, a wireless communication device and/or chipset (such as a Bluetooth™ device, an 502.11 device, a Wi-Fi device, a WiMAX device, an NFC device, cellular communication facilities, etc.), and/or similar communication interfaces. The communication interface 1230 may permit data to be exchanged with a network (such as the network described below, to name one example), other computer systems, and/or any other devices described herein. In many embodiments, the computer system 1200 will further comprise a non-transitory working memory 1235, which can include a RAM or ROM device, as described above.

The computer system 1200 also can comprise software elements, shown as being currently located within the working memory 1235, including an operating system 1240, device drivers, executable libraries, and/or other code, such as one or more application programs 1245, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such special/specific purpose code and/or instructions can be used to configure and/or adapt a computing device to a special purpose computer that is configured to perform one or more operations in accordance with the described methods.

A set of these instructions and/or code might be stored on a computer-readable storage medium, such as the storage device(s) 1225 described above. In some cases, the storage medium might be incorporated within a computer system, such as computer system 1200. In other embodiments, the storage medium might be separate from a computer system (e.g., a removable medium, such as a compact disc), and/or provided in an installation package, such that the storage medium can be used to program, configure and/or adapt a special purpose computer with the instructions/code stored thereon. These instructions might take the form of executable code, which is executable by the computer system 1200 and/or might take the form of source and/or installable code, which, upon compilation and/or installation on the computer system 1200 (e.g., using any of a variety of available compilers, installation programs, compression/decompression utilities, etc.) then takes the form of executable code.

Substantial variations may be made in accordance with specific requirements. For example, customized hardware might also be used, and/or particular elements might be implemented in hardware, software (including portable software, such as applets, etc.), or both. Moreover, hardware and/or software components that provide certain functionality can comprise a dedicated system (having specialized components) or may be part of a more generic system. For example, a risk management engine configured to provide some or all of the features described herein relating to the risk profiling and/or distribution can comprise hardware and/or software that is specialized (e.g., an application-specific integrated circuit (ASIC), a software method, etc.) or generic (e.g., processing unit 1210, applications 1245, etc.) Further, connection to other computing devices such as network input/output devices may be employed.

Some embodiments may employ a computer system (such as the computer system 1200) to perform methods in accordance with the disclosure. For example, some or all of the procedures of the described methods may be performed by the computer system 1200 in response to processing unit 1210 executing one or more sequences of one or more instructions (which might be incorporated into the operating system 1240 and/or other code, such as an application program 1245) contained in the working memory 1235. Such instructions may be read into the working memory 1235 from another computer-readable medium, such as one or more of the storage device(s) 1225. Merely by way of example, execution of the sequences of instructions contained in the working memory 1235 might cause the processing unit 1210 to perform one or more procedures of the methods described herein.

The terms "machine-readable medium" and "computer-readable medium," as used herein, refer to any medium that participates in providing data that causes a machine to operate in a specific fashion. In an embodiment implemented using the computer system 1200, various computer-readable media might be involved in providing instructions/code to processing unit 1210 for execution and/or might be used to store and/or carry such instructions/code (e.g., as signals). In many implementations, a computer-readable medium is a physical and/or tangible storage medium. Such a medium may take many forms, including but not limited to, non-volatile media, volatile media, and transmission media. Non-volatile media include, for example, optical and/or magnetic disks, such as the storage device(s) 1225. Volatile media include, without limitation, dynamic memory, such as the working memory 1235. Transmission media include, without limitation, coaxial cables, copper wire, and fiber optics, including the wires that comprise the bus 1205, as well as the various components of the communication interface 1230 (and/or the media by which the communication interface 1230 provides communication with other devices). Hence, transmission media can also take the form of waves (including without limitation radio, acoustic and/or light waves, such as those generated during radio-wave and infrared data communications).

Common forms of physical and/or tangible computer-readable media include, for example, a magnetic medium, optical medium, or any other physical medium with patterns of holes, a RAM, a PROM, EPROM, a FLASH-EPROM, any other memory chip or cartridge, a carrier wave as described hereinafter, or any other medium from which a computer can read instructions and/or code.

The communication interface 1230 (and/or components thereof) generally will receive the signals, and the bus 1205 then might carry the signals (and/or the data, instructions, etc. carried by the signals) to the working memory 1235, from which the processor(s) 1205 retrieves and executes the instructions. The instructions received by the working memory 1235 may optionally be stored on a non-transitory storage device 1225 either before or after execution by the processing unit 1210.

The methods, systems, and devices discussed above are examples. Some embodiments were described as processes depicted as flow diagrams or block diagrams. Although each may describe the operations as a sequential process, many of the operations can be performed in parallel or concurrently. In addition, the order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Processors may perform the associated tasks.

It should be noted that the systems and devices discussed above are intended merely to be examples. It must be stressed that various embodiments may omit, substitute, or add various procedures or components as appropriate. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known structures and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

The methods, systems, devices, graphs, and tables discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims. Additionally, the techniques discussed herein may provide differing results with different types of context awareness classifiers.

While illustrative and presently preferred embodiments of the disclosed systems, methods, and machine-readable media have been described in detail herein, it is to be understood that the inventive concepts may be otherwise variously embodied and employed, and that the appended claims are intended to be construed to include such variations, except as limited by the prior art.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate to in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate to in the context of the systems, devices, circuits, methods, and other implementations described herein. As used herein, including in the claims, "and" as used in a list of items prefaced by "at least one of" or "one or more of" indicates that any combination of the listed items may be used. For example, a list of "at least one of A, B, and C" includes any of the combinations A or B or C or AB or AC or BC and/or ABC (i.e., A and B and C). Furthermore, to the extent more than one occurrence or use of the items A, B, or C is possible, multiple uses of A, B, and/or C may form part of the contemplated combinations. For example, a list of "at least one of A, B, and C" may also include AA, AAB, AAA, BB, etc.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed is:

1. A method of parallel medication processing using an automated dosing device, the method comprising:
   receiving a request for preparation of at least one dosed medication delivery container with the automated dosing device, each of the at least one dosed medication delivery container comprising a medication delivery container and at least one ingredient added to the medication delivery container by the automated dosing device, the automated dosing device comprising a plurality of stations, wherein the at least one medication delivery container comprises at least: a syringe; and a medication bag;
   determining at least one attribute of the request for preparation of at least one dosed medication delivery container;
   identifying a template corresponding to the determined at least one attribute of the request for preparation of the at least one dosed medication delivery container, wherein the template identifies steps and an order of the steps for the filling of the dosed medication delivery container;
   executing the template, wherein executing the template comprises:
      iteratively assigning tasks to a plurality of stations within the automated dosing device, wherein at least some of the tasks are at least partially overlappingly performed by a plurality of stations; and
      directing a transport tool to move at least one medication delivery container between the stations of the automated dosing device.

2. The method of claim 1, wherein the at least one attribute comprises at least one of:
   a type of the at least one dosed medication delivery container;
   a number of ingredients in the at least one dosed medication delivery container;
   a source of at least one of the ingredients in the at least one dosed medication delivery container; and
   a dose size for each of the ingredients in the at least one dosed medication delivery container.

3. The method of claim 1, wherein at least partially overlappingly performing at least some of the tasks comprises simultaneously performing at least some of the tasks.

4. The method of claim 1, wherein the at least one medication delivery container comprises a plurality of individual syringes.

5. The method of claim 1, wherein the transport tool comprises a robotic arm configured to grab and manipulate the at least one medication delivery container.

6. The method of claim 5, wherein the transport tool further comprises a bag carousel.

7. The method of claim 6, wherein the bag carousel comprises: a circular member having an outer circumference; a plurality of slots sized to receive a medication bag, wherein the medication bag received in one of the plurality of slots is wholly retained within the outer circumference of the circular member; and at least one bag shuttle comprising a moveable member configured to remove the medication bag from the bag carousel.

8. The method of claim 1, wherein the plurality of stations comprise: a doser; a scale; at least one reconstitution mixer; a withdrawal station; and a syringe finisher.

9. The method of claim 8, wherein the scale comprises two or more syringe holders.

10. The method of claim 9, wherein the scale further comprises a medication bag holder, and wherein executing the template comprises determining a weight of a medication bag based on a plurality of weights of multiple medication delivery containers measured by the scale, wherein the multiple medication delivery containers include the medication bag and a syringe.

11. The method of claim 10, wherein executing the template comprises:
   filling a first syringe with a first medication with the doser; and
   dosing medication bags with a first medication, wherein dosing medication bags with the first medication comprises:
      transferring a first one of a plurality of medication bags from a bag carousel to the doser;
      injecting with the first syringe a dose of the first medication into the first one of the plurality of medication bags;
      transferring the first one of the plurality of medication bags from the doser to the bag carousel; and
      rotating the bag carousel in a first direction to position a first next one of the plurality of medication bags for transferring from the bag carousel to the doser.

12. The method of claim 11, wherein dosing the medication bags with the first medication comprises:
   measuring a first weight of the first one of the plurality of medication bags before injecting with the first syringe the dose of the first medication into the first one of the plurality of medication bags;

measuring a second weight of the first one of the plurality of medication bags after injecting with the first syringe the dose of the first medication into the first one of the plurality of medication bags; and determining a dosing of the first one of the plurality of medication bags based on the first weight and the second weight.

13. The method of claim 12, wherein executing the template further comprises:

filling a second syringe with a second medication with the doser; and dosing medication bags with the second medication, wherein dosing medication bags with the second medication comprises:

transferring a second one of the plurality of medication bags from the bag carousel to the doser;

injecting with the second syringe a second dose of the second medication into the second one of the plurality of medication bags;

transferring the second one of the plurality of medication bags from the doser to the bag carousel; and rotating the bag carousel in a second direction to position a second next one of the plurality of medication bags for transferring from the bag carousel to the doser.

14. The method of claim 9, wherein executing the template comprises:

controlling the transport tool to place an empty, first syringe in a first syringe holder;

measuring and storing a first weight with the scale, the first weight corresponding to the weight of the empty, first syringe;

controlling the transport tool to place the empty, first syringe in the doser for filling and an empty, second syringe in the first syringe holder;

measuring and storing a second weight with the scale, the second weight corresponding to the weight of the empty, second syringe;

filling the first syringe with the doser;

controlling the transport tool to retrieve the filled, first syringe from the doser and place the filled, first syringe in a second syringe holder; and measuring and storing a third weight with the scale, the third weight corresponding to the weight of the filled, first syringe and of the empty, second syringe.

15. The method of claim 14, wherein executing the template further comprises determining a weight of the filled, first syringe by determining a difference between the third weight and the second weight.

16. The method of claim 15, wherein executing the template further comprises determining a dosing of the first syringe by determining a difference between the weight of the filled, first syringe and the first weight.

17. The method of claim 1, wherein the request for preparation of the at least one dosed medication delivery container with the automated dosing device comprises a request for preparation of a plurality of dosed medication delivery containers.

18. The method of claim 17, further comprising: dividing the request for preparation of the plurality of dosed medication delivery containers into a plurality of mini-batches, wherein processing each of the mini-batches causes preparation of a subset of the plurality of dosed medication delivery containers; and processing each of the mini-batches.

19. The method of claim 18, wherein each of the mini-batches are serially processed.

20. The method of claim 18, wherein dividing the request for preparation of the plurality of dosed medication delivery containers into the plurality of mini-batches comprises: identifying a size for the mini-batches; and creating the plurality of mini-batches of the identified size.

21. The method of claim 20, wherein identifying the size for the mini-batches comprises:

identifying ingredients and dosing of the ingredients for preparation of each of the plurality of dosed medication delivery containers;

identifying a vial size for each of the ingredients;

determining a maximum number of doses for each of the ingredients; and setting the size for the mini-batch at the largest of the maximum number of doses for each of the ingredients.

22. An automated dosing device comprising:

a plurality of stations, wherein each of the plurality of stations comprises a station controller and station hardware, wherein each station controller is configured to control station hardware to perform an operation;

a transport tool configured to transport medication delivery containers to and from the plurality of stations; and a central controller comprising a processor configured to:

receive a request for preparation of at least one dosed medication delivery container, each of the at least one dosed medication delivery container comprising a medication delivery container at least partially filled by at least one ingredient, wherein the medication delivery container comprises at least: a syringe; and a medication bag;

determine at least one attribute of the request for preparation of at least one dosed medication delivery container;

identify a template corresponding to the determined at least one attribute of the request for preparation of the at least one dosed medication delivery container, wherein the template identifies steps and an order of the steps for the filling of the dosed medication delivery container;

execute the template, wherein executing the template comprises:

iteratively assign tasks to at least some of the plurality of stations, wherein at least some of the tasks are at least partially overlappingly performed; and direct a transport tool to move at least one medication delivery container between the stations.

23. The device of claim 22, wherein the at least one attribute comprises at least one of:

a type of the at least one dosed medication delivery container;

a number of ingredients in the at least one dosed medication delivery container;

a source of at least one of the ingredients in the at least one dosed medication delivery container; and a dose size for each of the ingredients in the at least one dosed medication delivery container.

24. The device of claim 22, wherein at least partially overlappingly performing at least some of the tasks comprises simultaneously performing at least some of the tasks.

25. The device of claim 22, wherein the at least one medication delivery container comprises a plurality of individual syringes.

26. The device of claim 22, wherein the transport tool comprises: a robotic arm configured to grab and manipulate the at least one medication delivery container; and a bag carousel.

27. The device of claim 26, wherein the bag carousel comprises: a circular member having an outer circumference; a plurality of slots sized to receive a medication bag, wherein the medication bag received in one of the plurality of slots is wholly retained within the outer circumference of the circular member; and at least one bag shuttle comprising a moveable member configured to remove the medication bag from the bag carousel.

28. The device of claim 22, wherein the plurality of stations comprise: a doser; a scale; at least one reconstitution mixer; a withdrawal station; and a syringe finisher.

29. The device of claim 28, wherein the scale comprises two or more syringe holders.

30. The device of claim 29, wherein the scale further comprises a medication bag holder, and wherein executing the template comprises determining a weight of a medication bag based on a plurality of weights of multiple medication delivery containers measured by the scale, wherein the multiple medication delivery containers include the medication bag and a syringe.

31. The device of claim 30, wherein executing the template comprises:
filling a first syringe with a first medication with the doser; and
dosing medication bags with a first medication, wherein dosing medication bags with the first medication comprises:
transferring a first one of a plurality of medication bags from a bag carousel to the doser;
injecting with the first syringe a dose of the first medication into the first one of the plurality of medication bags;
transferring the first one of the plurality of medication bags from the doser to the bag carousel; and
rotating the bag carousel in a first direction to position a first next one of the plurality of medication bags for transferring from the bag carousel to the doser.

32. The device of claim 31, wherein dosing the medication bags with the first medication comprises:
measuring a first weight of the first one of the plurality of medication bags before injecting with the first syringe the dose of the first medication into the first one of the plurality of medication bags;
measuring a second weight of the first one of the plurality of medication bags after injecting with the first syringe the dose of the first medication into the first one of the plurality of medication bags; and
determining a dosing of the first one of the plurality of medication bags based on the first weight and the second weight.

33. The device of claim 32, wherein executing the template further comprises:
filling a second syringe with a second medication with the doser; and
dosing medication bags with the second medication, wherein dosing medication bags with the second medication comprises:
transferring a second one of the plurality of medication bags from the bag carousel to the doser;
injecting with the second syringe a second dose of the second medication into the second one of the plurality of medication bags;
transferring the second one of the plurality of medication bags from the doser to the bag carousel; and
rotating the bag carousel in a second direction to position a second next one of the plurality of medication bags for transferring from the bag carousel to the doser.

34. The device of claim 29, wherein executing the template comprises:
controlling the transport tool to place an empty, first syringe in a first syringe holder;
measuring and storing a first weight with the scale, the first weight corresponding to the weight of the empty, first syringe;
controlling the transport tool to place the empty, first syringe in the doser for filling and an empty, second syringe in the first syringe holder;
measuring and storing a second weight with the scale, the second weight corresponding to the weight of the empty, second syringe;
filling the first syringe with the doser;
controlling the transport tool to retrieve the filled, first syringe from the doser and place the filled, first syringe in a second syringe holder; and
measuring and storing a third weight with the scale, the third weight corresponding to the weight of the filled, first syringe and of the empty, second syringe.

35. The device of claim 34, wherein executing the template further comprises determining a weight of the filled, first syringe by determining a difference between the third weight and the second weight.

36. The device of claim 35, wherein executing the template further comprises determining a dosing of the first syringe by determining a difference between the weight of the filled, first syringe and the first weight.

37. The device of claim 22, wherein the request for preparation of the at least one dosed medication delivery container comprises a request for preparation of a plurality of dosed medication delivery containers.

38. The device of claim 37, wherein the processor is further configured to: divide the request for preparation of the plurality of dosed medication delivery containers into a plurality of mini-batches, wherein processing each of the mini-batches causes preparation of a subset of the plurality of dosed medication delivery containers; and direct processing each of the mini-batches.

39. The device of claim 38, wherein each of the mini-batches are serially processed.

40. The device of claim 38, wherein dividing the request for preparation of the plurality of dosed medication delivery containers into the plurality of mini-batches comprises: identifying a size for the mini-batches; and creating the plurality of mini-batches of the identified size.

41. The device of claim 40, wherein identifying the size for the mini-batches comprises:
identifying ingredients and dosing of the ingredients for preparation of each of the plurality of dosed medication delivery containers;
identifying a vial size for each of the ingredients;
determining a maximum number of doses for each of the ingredients; and
setting the size for the mini-batch at the largest of the maximum number of doses for each of the ingredients.

* * * * *